US012096957B2

(12) United States Patent  (10) Patent No.: US 12,096,957 B2
Hochman et al.  (45) Date of Patent: Sep. 24, 2024

(54) DEVICE AND METHOD FOR NEEDLE/CATHETER LOCATION UTILIZING CORRELATION ANALYSIS

(71) Applicant: Milestone Scientific Inc., Roseland, NJ (US)

(72) Inventors: Mark N. Hochman, Lake Success, NY (US); Richard K. Buck, Crystal Lake, IL (US)

(73) Assignee: MILESTONE SCIENTIFIC, INC., Roseland, NJ (US)

( * ) Notice: Subject to any disclaimer, the term of this patent is extended or adjusted under 35 U.S.C. 154(b) by 21 days.

(21) Appl. No.: 17/583,417

(22) Filed: Jan. 25, 2022

(65) Prior Publication Data

US 2022/0378318 A1  Dec. 1, 2022

Related U.S. Application Data

(63) Continuation of application No. 16/858,094, filed on Apr. 24, 2020, now abandoned.

(51) Int. Cl.
*A61B 17/34*  (2006.01)
*A61B 5/00*  (2006.01)
(Continued)

(52) U.S. Cl.
CPC ........ *A61B 17/3403* (2013.01); *A61B 5/0215* (2013.01); *A61B 5/0261* (2013.01); *A61B 5/061* (2013.01); *A61B 5/7246* (2013.01); *A61B 5/7425* (2013.01); *A61B 5/743* (2013.01); *A61B 5/746* (2013.01); *A61B 34/76* (2016.02); *A61M 25/0105* (2013.01); *A61B 5/02438* (2013.01);
(Continued)

(58) Field of Classification Search
CPC ............... A61B 17/3403; A61B 34/76; A61B 2017/00199; A61M 25/0105; A61M 2025/0166
See application file for complete search history.

(56) References Cited

U.S. PATENT DOCUMENTS 3,867,934 A  2/1975  Ollivier
4,356,826 A  11/1982  Kubota
(Continued)

FOREIGN PATENT DOCUMENTS

CN  104394905  3/2015
DE  202005019430  2/2006
(Continued)

OTHER PUBLICATIONS

Wikipedia—Cross correlation "https://en.wikipedia.org/wiki/Cross-correlation" Accessed Oct. 5, 2023 (Year: 2023).*
(Continued)

*Primary Examiner* — Carl H Layno
*Assistant Examiner* — Manolis Pahakis
(74) *Attorney, Agent, or Firm* — Niels Haun; Dann, Dorfman, Herrell and Skillman, P. C.

(57) ABSTRACT

An apparatus and method to enable clinicians to verify needle or catheter location within an anatomic site by relying upon combined sensing of two signals, such as a pressure signal and a heart rate pulse signal, in which the detection of a correlation between both signals is identified to confirm location of the needle or catheter.

33 Claims, 9 Drawing Sheets

(51) Int. Cl.
  *A61B 5/0215* (2006.01)
  *A61B 5/024* (2006.01)
  *A61B 5/026* (2006.01)
  *A61B 5/06* (2006.01)
  *A61B 17/00* (2006.01)
  *A61B 34/00* (2016.01)
  *A61B 90/00* (2016.01)
  *A61M 25/00* (2006.01)
  *A61M 25/01* (2006.01)

(52) U.S. Cl.
  CPC ... *A61B 5/6826* (2013.01); *A61B 2017/00039* (2013.01); *A61B 2017/00057* (2013.01); *A61B 2017/00115* (2013.01); *A61B 2017/00199* (2013.01); *A61B 2090/064* (2016.02); *A61M 2025/0003* (2013.01); *A61M 2025/0166* (2013.01)

(56) References Cited

U.S. PATENT DOCUMENTS

| | | |
|---|---|---|
| 4,403,988 A | 9/1983 | Binard |
| 4,518,383 A | 5/1985 | Evans |
| 4,624,659 A | 11/1986 | Goldberg |
| 4,679,567 A | 7/1987 | Hanlon |
| 4,790,821 A | 12/1988 | Stines |
| 4,801,293 A | 1/1989 | Jackson |
| 4,893,630 A | 1/1990 | Bray, Jr. |
| 4,988,337 A | 1/1991 | Ito |
| 4,998,914 A | 3/1991 | Wiest |
| 5,100,390 A | 3/1992 | Lubeck |
| 5,178,603 A | 1/1993 | Prince |
| 5,197,895 A | 3/1993 | Stupecky |
| 5,267,565 A | 12/1993 | Beard |
| 5,269,762 A | 12/1993 | Armbruster |
| 5,295,967 A | 3/1994 | Rondelet |
| D348,101 S | 6/1994 | Poli |
| 5,378,231 A | 1/1995 | Johnson |
| 5,405,269 A | 4/1995 | Stupecky |
| D360,259 S | 7/1995 | Ijiri |
| 5,520,650 A | 5/1996 | Zadini |
| 5,611,778 A | 3/1997 | Brinon |
| 5,660,567 A | 8/1997 | Nierlich |
| 5,681,285 A | 10/1997 | Ford |
| 5,690,618 A | 11/1997 | Smith |
| D390,654 S | 2/1998 | Alsberg |
| 5,727,553 A | 3/1998 | Saad |
| 5,810,770 A | 9/1998 | Chin |
| D409,148 S | 5/1999 | Yotsutani |
| 5,902,273 A | 5/1999 | Yang |
| 5,954,701 A | 9/1999 | Matalon |
| 5,980,463 A | 11/1999 | Brockway |
| 6,022,337 A | 2/2000 | Herbst |
| 6,024,576 A | 2/2000 | Bevirt |
| 6,120,457 A | 9/2000 | Coombes |
| 6,126,610 A | 10/2000 | Rich |
| 6,159,161 A | 12/2000 | Hodosh |
| D436,927 S | 1/2001 | Hogan |
| 6,200,289 B1 | 3/2001 | Hochman |
| 6,456,874 B1 | 9/2002 | Hafer |
| 6,468,241 B1 | 10/2002 | Gelfand |
| 6,569,147 B1 | 5/2003 | Evans |
| 6,652,482 B2 | 11/2003 | Hochman |
| 6,695,806 B2 | 2/2004 | Gelfand |
| 6,705,990 B1 | 3/2004 | Gallant |
| 6,716,192 B1 | 4/2004 | Orosz, Jr. |
| 6,773,417 B2 | 8/2004 | Fitzgibbons |
| 6,786,885 B2 | 9/2004 | Hochman |
| 6,866,648 B2 | 3/2005 | Hadzic |
| 6,887,216 B2 | 5/2005 | Hochman |
| 6,942,637 B2 | 9/2005 | Cartledge |
| 7,022,072 B2 | 4/2006 | Fox |
| 7,198,602 B2 | 4/2007 | Eide |
| 7,285,100 B2 | 10/2007 | Lemaire |
| D556,910 S | 12/2007 | Reihanifam |
| 7,335,162 B2 | 2/2008 | Eide |
| 7,364,570 B2 | 4/2008 | Gerondale |
| 7,395,214 B2 | 7/2008 | Shillingburg |
| 7,449,008 B2 | 11/2008 | Hochman |
| D600,644 S | 9/2009 | Leung |
| 7,604,602 B2 | 10/2009 | Roteliuk |
| 7,618,409 B2 | 11/2009 | Hochman |
| 7,635,338 B2 | 12/2009 | Eide |
| 7,641,637 B2 | 1/2010 | Gerondale |
| 7,727,224 B2 | 6/2010 | Hadzic |
| 7,775,985 B2 | 8/2010 | Eide |
| D630,727 S | 1/2011 | Petrovic |
| 7,896,833 B2 | 3/2011 | Hochman |
| 7,922,689 B2 | 4/2011 | Lechner |
| D642,984 S | 8/2011 | Sasaki |
| 8,002,736 B2 | 8/2011 | Patrick |
| 8,016,763 B2 | 9/2011 | Eide |
| 8,079,976 B2 | 12/2011 | Patrick |
| 8,137,312 B2 | 3/2012 | Sundar |
| 8,142,414 B2 | 3/2012 | Patrick |
| 8,197,443 B2 | 6/2012 | Sundar |
| 8,256,984 B2 | 9/2012 | Fathallah |
| 8,262,584 B2 | 9/2012 | Eide |
| D669,096 S | 10/2012 | Katsura |
| D669,165 S | 10/2012 | Estes |
| 8,282,565 B2 | 10/2012 | Mahapatra |
| 8,308,654 B2 | 11/2012 | Eide |
| 8,398,564 B2 | 3/2013 | Eide |
| D679,379 S | 4/2013 | Katsura |
| 8,444,592 B2 | 5/2013 | Williams |
| 8,480,630 B2 | 7/2013 | Mudd |
| D687,536 S | 8/2013 | Guarraia |
| 8,545,440 B2 | 10/2013 | Patrick |
| 8,562,600 B2 | 10/2013 | Kirkpatrick |
| 8,597,193 B2 * | 12/2013 | Grunwald ............ A61B 8/0841<br>600/468 |
| 8,684,947 B2 | 4/2014 | Eide |
| 8,764,668 B2 | 7/2014 | Roteliuk |
| 8,781,555 B2 * | 7/2014 | Burnside ................ A61B 46/00<br>600/585 |
| 8,814,807 B2 | 8/2014 | Hulvershorn |
| 8,834,506 B2 * | 9/2014 | Alhumaid .......... A61B 17/3478<br>604/506 |
| 8,896,324 B2 | 11/2014 | Kroh |
| 8,926,525 B2 | 1/2015 | Hulvershorn |
| 8,992,481 B2 | 3/2015 | Mudd |
| 8,998,841 B2 | 4/2015 | Shen |
| D730,514 S | 5/2015 | Boaz |
| 9,044,542 B2 | 6/2015 | Patrick |
| D734,475 S | 7/2015 | Ross |
| 9,084,550 B1 | 7/2015 | Bartol |
| D736,370 S | 8/2015 | Sabin |
| D741,811 S | 10/2015 | Hochman |
| 9,199,044 B2 | 12/2015 | Bangera |
| 9,205,204 B2 | 12/2015 | Bangera |
| 9,358,038 B2 | 6/2016 | Hulvershorn |
| 9,358,350 B2 | 6/2016 | Bangera |
| D760,888 S | 7/2016 | Friedrich |
| D765,832 S | 9/2016 | Hochman |
| 9,443,446 B2 | 9/2016 | Rios |
| 9,452,261 B2 | 9/2016 | Alon |
| 9,468,396 B2 | 10/2016 | Mahapatra |
| 9,504,790 B1 | 11/2016 | Hochman |
| 9,603,537 B2 | 3/2017 | Lechner |
| 9,642,534 B2 | 5/2017 | Mahapatra |
| 9,655,528 B2 | 5/2017 | Zhu |
| D801,519 S | 10/2017 | Sabin |
| D803,386 S | 11/2017 | Sabin |
| D803,387 S | 11/2017 | Bodwell |
| 9,888,881 B2 | 2/2018 | Hulvershorn |
| 9,901,679 B2 | 2/2018 | Shen |
| 9,956,341 B2 | 5/2018 | Hockman |
| 10,004,450 B2 | 6/2018 | Moskowitz |
| 10,117,673 B2 | 11/2018 | Luo |
| 10,220,180 B2 | 3/2019 | Hochman |
| 10,383,610 B2 | 8/2019 | Moskowitz |
| D859,634 S | 9/2019 | Hochman |
| 10,406,285 B2 | 9/2019 | Anand |

(56) References Cited

U.S. PATENT DOCUMENTS

| | | | |
|---|---|---|---|
| 10,463,838 B2 | 11/2019 | Hulvershorn | |
| 10,602,958 B2 | 3/2020 | Silverstein | |
| 10,632,255 B2 | 4/2020 | Hochman | |
| 10,646,660 B1 | 5/2020 | Hochman | |
| 10,842,966 B2 | 11/2020 | Hochman | |
| 10,946,139 B2 | 3/2021 | Hochman | |
| 10,960,141 B1 | 3/2021 | Hochman | |
| 11,058,354 B2* | 7/2021 | Mahapatra | A61B 5/4887 |
| 11,134,984 B2* | 10/2021 | Nikolski | A61B 17/320016 |
| 11,147,927 B2 | 10/2021 | Hochman | |
| 11,471,595 B2 | 10/2022 | Hochman | |
| 2002/0016567 A1 | 2/2002 | Hochman | |
| 2002/0016569 A1 | 2/2002 | Critchlow | |
| 2002/0022807 A1 | 2/2002 | Duchon | |
| 2002/0143294 A1 | 10/2002 | Duchon | |
| 2003/0014006 A1 | 1/2003 | Alexandre | |
| 2004/0033477 A1* | 2/2004 | Ramphal | G09B 23/306 |
| | | | 434/272 |
| 2004/0035743 A1 | 2/2004 | Tighe | |
| 2004/0044292 A1 | 3/2004 | Yasushi | |
| 2004/0149282 A1 | 8/2004 | Hickle | |
| 2004/0215080 A1 | 10/2004 | Lechner | |
| 2005/0004513 A1 | 1/2005 | Beyerlein | |
| 2005/0004514 A1 | 1/2005 | Hochman | |
| 2005/0096593 A1 | 5/2005 | Pope | |
| 2005/0126304 A1 | 6/2005 | Sparks | |
| 2006/0122555 A1 | 6/2006 | Hochman | |
| 2006/0247657 A1 | 11/2006 | Trieu | |
| 2007/0038143 A1 | 2/2007 | Christensen | |
| 2007/0055142 A1* | 3/2007 | Webler | A61B 5/704 |
| | | | 600/425 |
| 2007/0197922 A1 | 8/2007 | Bradley | |
| 2008/0058702 A1 | 3/2008 | Arndt | |
| 2008/0103408 A1 | 5/2008 | Denton | |
| 2008/0281265 A1 | 11/2008 | Hochman | |
| 2009/0131832 A1 | 5/2009 | Sacristan Rock | |
| 2009/0149911 A1 | 6/2009 | Dacey, Jr. | |
| 2009/0149912 A1 | 6/2009 | Dacey, Jr. | |
| 2009/0171191 A1 | 7/2009 | Patrick | |
| 2009/0210029 A1 | 8/2009 | Tsui | |
| 2009/0221914 A1 | 9/2009 | Barrett | |
| 2009/0326482 A1 | 12/2009 | Hochman | |
| 2010/0022918 A1 | 1/2010 | Fujie | |
| 2010/0030102 A1 | 2/2010 | Poston | |
| 2010/0049270 A1 | 2/2010 | Pastore | |
| 2010/0056932 A1 | 3/2010 | Roteliuk | |
| 2010/0179488 A1 | 7/2010 | Spiegel | |
| 2010/0274191 A1 | 10/2010 | Ting | |
| 2011/0021905 A1 | 1/2011 | Patrick | |
| 2011/0046477 A1 | 2/2011 | Hulvershorn | |
| 2011/0054353 A1 | 3/2011 | Hulvershorn | |
| 2011/0060229 A1 | 3/2011 | Hulvershorn | |
| 2011/0087166 A1 | 4/2011 | Davis | |
| 2011/0112511 A1 | 5/2011 | Singer | |
| 2011/0120566 A1 | 5/2011 | Ohmi | |
| 2011/0190596 A1 | 8/2011 | Hacker | |
| 2011/0270179 A1 | 11/2011 | Ouyang | |
| 2011/0288481 A1 | 11/2011 | Mudd | |
| 2011/0298628 A1 | 12/2011 | Vad | |
| 2011/0301500 A1 | 12/2011 | Maguire | |
| 2012/0022407 A1 | 1/2012 | Lechner | |
| 2012/0083760 A1 | 4/2012 | Ledford | |
| 2012/0101410 A1 | 4/2012 | Lechner | |
| 2012/0232389 A1 | 9/2012 | Guzman | |
| 2012/0259237 A1 | 10/2012 | Axelrod | |
| 2012/0283582 A1 | 11/2012 | Mahapatra | |
| 2012/0289819 A1 | 11/2012 | Snow | |
| 2012/0296176 A1 | 11/2012 | Herbst | |
| 2012/0310052 A1* | 12/2012 | Mahapatra | A61B 17/3403 |
| | | | 600/301 |
| 2013/0041258 A1 | 2/2013 | Patrick | |
| 2013/0046190 A1 | 2/2013 | Davies | |
| 2013/0053851 A1 | 2/2013 | Schmitz | |
| 2013/0131633 A1 | 5/2013 | Mudd | |
| 2013/0261533 A1 | 10/2013 | Norkunas | |
| 2014/0012226 A1 | 1/2014 | Hochman | |
| 2014/0066891 A1 | 3/2014 | Burns | |
| 2014/0121636 A1 | 5/2014 | Boyden | |
| 2014/0121637 A1 | 5/2014 | Boyden | |
| 2014/0207050 A1 | 7/2014 | Gonzalez | |
| 2014/0221965 A1 | 8/2014 | Regittnig | |
| 2014/0316268 A1 | 10/2014 | Kafiluddi | |
| 2014/0343406 A1 | 11/2014 | Damjanovic | |
| 2015/0025363 A1 | 1/2015 | Hulvershorn | |
| 2015/0150519 A1 | 6/2015 | Glenn | |
| 2015/0283365 A1 | 10/2015 | Dacey, Jr. | |
| 2015/0374929 A1 | 12/2015 | Hyde | |
| 2016/0135712 A1 | 5/2016 | Holochwost | |
| 2016/0136363 A1 | 5/2016 | McClellan | |
| 2016/0228633 A1 | 8/2016 | Welsch | |
| 2017/0106142 A1 | 4/2017 | Hochman | |
| 2017/0106163 A1 | 4/2017 | Hochman | |
| 2017/0188832 A1 | 7/2017 | Lechner | |
| 2018/0064870 A1 | 3/2018 | Hochman | |
| 2018/0087517 A1 | 3/2018 | Glenn | |
| 2018/0116551 A1 | 5/2018 | Newman | |
| 2018/0228968 A1 | 8/2018 | Hochman | |
| 2018/0296792 A1 | 10/2018 | Hochman | |
| 2018/0318501 A1 | 11/2018 | Hochman | |
| 2021/0085889 A1 | 3/2021 | Hochman | |
| 2021/0170110 A1 | 6/2021 | Hochman | |
| 2021/0290843 A1 | 9/2021 | Hochman | |
| 2021/0330349 A1 | 10/2021 | Hochman | |
| 2023/0233168 A1* | 7/2023 | Chen | A61B 5/026 |
| | | | 600/424 |

FOREIGN PATENT DOCUMENTS

| | | |
|---|---|---|
| EP | 0303824 | 2/1989 |
| EP | 0538259 | 4/1993 |
| FR | 2628625 | 9/1989 |
| HU | P8806113 | 10/1990 |
| HU | P0204296 | 3/2003 |
| JP | 5042218 | 2/1993 |
| JP | 6007440 | 1/1994 |
| JP | 6142114 | 5/1994 |
| WO | 1996005768 | 2/1996 |
| WO | 9725081 | 7/1997 |
| WO | 03000146 | 1/2003 |
| WO | 2010071416 | 6/2010 |
| WO | 2014097301 | 6/2014 |
| WO | 2016128985 | 8/2016 |
| WO | 2017066732 | 4/2017 |
| WO | 2018152225 | 8/2018 |
| WO | 2018204668 | 11/2018 |

OTHER PUBLICATIONS

International Search Report and Written Opinion issued in International Application No. PCT/US16/57264 on Mar. 22, 2017.

Usubiaga et al., "Epidural Pressure and Its Relation to Spread of Anesthetic Solutions in Epidural Space", Anesthesia and Analgesia, vol. 46, No. 4, pp. 440-446, 1967.

Husemeyer et al., "Lumbar Extradural Injection Pressures N Pregnant Women", British Journal of Anaesthesia, 52, pp. 55-59, 1980.

Paul et al., "Extradural Pressure Following the Injection of Two Volume of Bupivacaine", British Journal of Anaesthesia, 62, pp. 368-372, 1989.

Hirabayashi et al., "Effect of Extradural Compliance and Resistance on Spread of Extradural Analgesia", British Journal of Anaesthesia, 65, pp. 508-513, 1990.

Abstract of: Vas, "A study of epidural pressures in infants", Pediatric Anaesthesia, 11 (5), pp. 575-583, 2001.

Lechner et al., "Clinical results with a new acoustic device to identify the epidural space", Anesthesia, 57, pp. 768-772, 2002.

Gadsden et al., "Opening Injection Pressure Consistently Detects Needle-Nerve Contact during Ultrasound-guided Interscalene Brachial Plexus Block" Anesthesiology, vol. 120, No. 5, May 2014, pp. 1246-1253.

Cohen et al., "Functional deficits after intraneural injection during interscalene block", Regional Anesthesia and Pain Medicine, vol. 35, No. 4, Jul.-Aug. 2010, pp. 397-399.

(56) References Cited

OTHER PUBLICATIONS

Reiss et al., "Nerve injury complicating ultrasound/electrostimulation-guided supraclavicular brachial plexus block", Regional Anesthesia and Pain Medicine, vol. 35, No. 4, Jul.-Aug. 2010, pp. 400-401.

Lupu et al., "Nerve expansion seen on ultrasound predicts histologic but not functional nerve injury after intraneural injection in pigs", Regional Anesthesia and Pain Medicine, vol. 35, No. 2, Mar.-Apr. 2010, pp. 132-139.

Steinfeldt et al., "Histological consequences of needle-nerve contact following nerve stimulation in a pig model", Anesthesiology Research and Practice, vol. 2011, Feb. 2011, 9 pages.

Steinfeldt et al., "Forced needle advancement during needle-nerve contact in a porcine model: Histological outcome", Anesthesia & Analgesia, vol. 113, No. 2, Aug. 2011, pp. 417-420.

Sites et al., "Characterizing novice behavior associated with learning ultrasound-guided peripheral regional anesthesia", Regional Anesthesia and Pain Medicine, vol. 32, No. 2, Mar.-Apr. 2007, pp. 107-115.

Sites et al., "Incidence of local anesthetic systemic toxicity and postoperative neurologic symptoms associated with 12,668 ultrasound-guided nerve blocks", Regional Anesthesia and Pain Medicine, vol. 37, No. 5, Sep.-Oct. 2012, pp. 478-482.

Liu et al., "Incidence of unintentional intraneural injection and postoperative neurological complications with ultrasound-guided interscalene and supraclavicular nerve blocks", Anaesthesia vol. 66, 2011, pp. 168-174.

Abstract of: Bilbao et al., "Neurological complications associated with ultrasound-guided interscalene and supraclavicular block in elective surgery of the shoulder and arm. Prospective observational study in a university hospital", Rev Esp Anestesiol Reanim, vol. 60, No. 7, Aug.-Sep. 2013, pp. 384-391.

Widmer et al., "Incidence and severity of complications due to femoral nerve blocks performed for knee surgery", The Knee, Nov. 2012, 5 pages.

Hadzic et al., "Combination of intraneural injection and high injection pressure leads to fascicular injury and neurologic deficits in dogs", Regional Anesthesia and Pain Medicine, vol. 29 No. 5 Sep.-Oct. 2004, pp. 417-423.

Kapur et al., "Neurologic and histologic outcome after intraneural injections of lidocaine in canine sciatic nerves", ACTA, Anaesthesiologica Scandinavica, vol. 51, 2007, pp. 101-107.

International Preliminary Report on Patentability issued in International Patent Application No. PCT/US16/57264 on Apr. 17, 2018.

"Medical Device Sanity"; http://mdgoo.blogspot.com/2014/12/another-medical-device-supplier-with.html; published prior to Oct. 27, 2017.

Al-Aamri, et al., "Reliability of Pressure Waveform Analysis to Determine Correct Epidural Needle Placement in Labouring Women", Anaesthesia 2017, 72, pp. 840-844.

Cohen et al, "Epidural Block for Obstetrics: Comparison of Bolus Injection of Local Anesthetic with Gravity Flow Technique", Journal of Clinical Anesthesia, 9, 1997, pp. 623-528.

Cohen et al, "Extradural Block in Obstetric Patients: Review of Experience with Gravity Administration", Acta Anaesthesiologica Scandinavica, 35, 1991, pp. 676-679.

Dawkins, "The identification of the epidural space" Anaesthesia, vol. 18, No. 1, Jan. 1963, pp. 66-77.

Examination Report issued in Australian Patent Application No. 2013287174 on Oct. 26, 2016.

Extended European Search Report issued in EP Application No. 13813314.5 dated Feb. 18, 2016.

Gadsden, et al., "High Opening Injection Pressure is Associated With Needle-Nerve and Needle-Fascia Contact During Femoral Nerve Block", Regional Anesthesia and Pain Medicine, vol. 41, No. 1, Jan.-Feb. 2016, pp. 50-55.

Ghelber et al., "Identification of the Epidural Space Using Pressure Measurement . . . ", Regional Anesthesia and Pain Medicine, vol. 33, No. 4, Jul.-Aug. 2008, pp. 346-352.

Ghia, et al, "Confirmation of Location of Epidural Catheters by Epidural Pressure Waveform and Computed Tomography Cathetergram", Regional Anesthesia and Pain Medicine, vol. 26, No. 4 (Jul.-Aug.), 2001, pp. 337-341.

Gong et al, "Pressure Waveform-Guided Epidural Catheter Placement in Comparison to the Loss-of-Resistance Conventional Method", Journal of Clinical Anesthesia, 26 (2014) pp. 395-401.

Hettiarachchi et al, "The Effect of Pulsatile Flow on Intrathecal Drug Delivery in the Spinal Canal", Annals of Biomedical Engineering, vol. 39, No. 10, Oct. 2011, pp. 2592-2602.

Hilber et al., "A systematic review of the diagnostic accuracy of epidural wave form analysis to identify the epidural space in surgical and labor patients", http://www.minervamedica.it, Minerva Anestesiologica, Apr. 2019, 85(4), pp. 393-400.

Hong et al, "Analysis of Epidural Waveform for Cervical Epidural Steroid Injections Confirmed with Fluoroscopy", An.md-journal.com, Hong and Jung Medicine (2018) 97:13, 4 pages.

Hsu et al, "The Frequency and Magnitude of Cerebrospinal Fluid Pulsations Influence Intrathecal Drug Distribution: Key Factors for Interpatient Variability", www.anesthesia-analgesia.org, vol. 115, No. 2, Aug. 2012, pp. 386-394.

http://www.anteis.com/AestheticDermatology/injectionsystem.php, published prior to Feb. 15, 2017.

http://www.intranixtech.com/myoguide-system/, published prior to Feb. 15, 2017.

https://www.dermaqueen.co.ki7, published prior to Feb. 15, 2017.

Hungarian Novelty Report for Application No. P 04 00176.

Iff et al., "The Use of an Acoustic Device to Identify the Epidural Space in Cattle", The Veterinary Journal, 187 (2011) pp. 267-268.

Iff et al., "The Use of an Acoustic Device to Identify the Extradural Space in Standing Horses", Veterinary Anaesthesia and Analgesia, 37 (2010) pp. 57-62.

Iff, Isabelle, et al., "The use of an acoustic device to identify the extradural space in standing horses", Veterinary Anaesthesia and Analgesia, 2010, 37, 57-62.

International Preliminary Report on Patentability for PCT/US2013/045142 Filed on Jun. 11, 2013.

International Preliminary Report on Patentability issued in International Application No. PCT/US06/29091 on Feb. 28, 2008.

International Preliminary Report on Patentability issued in International Application No. PCT/US13/45142 on Jan. 15, 2015.

International Search Report & Written Opinion issued in International Application No. PCT/US13/45142 on Sep. 10, 2013.

International Search Report and Written Opinion issued in International Application No. PCT/US18/31096 on Sep. 10, 2018.

International Search Report and Written Opinion issued in PCT/US16/63861 dated Mar. 6, 2017.

Jonathan Dillon, "Embedded storage in disposable medical items"; Article posted on Aug. 1, 2011; https://www.electronicproducts.com/Digital_ICs/Memory/Embedded_storage_in_disposable_medical_items.aspx.

Lechner et al., "Clinical Results with the Acoustic Puncture Assist Device, a New Acoustic Device to Identify the Epidural Space", Anesthesia Analgesia, (2003) pp. 1183-1187.

Lechner et al., "Thoracic Epidural Puncture Guided by an Acoustic Signal: Clinical Results", European Journal of Anesthesiology, 21 (2004) pp. 694-699.

Lechner, T.J.M. et al., "The use of a sound-enabled device to measure pressure during insertion of an epidural catheter in women in labour", Anaesthesia, 2011, 66, pp. 568-573.

Lennox et al, "A Pulsatile Pressure Waveform is a Sensitive Marker for Confirming the Location of the Thoracic Epidural Space", Journal of Cardiothoracic and Vascular Anesthesia, vol. 20, No. 5 Oct. 2006, pp. 659-663.

Leurcharusmee et al, "Reliability of Waveform Analysis as an Adjunct to Loss of Resistance for Thoracic Epidural Blocks", Regional Anesthesia and Pain Medicine, vol. 40, No. 6, Nov.-Dec. 2015, pp. 694-697.

Maxim Integrated Product Specification for DS28EC20 20Kb 1-Wire EEPROM; published prior to Oct. 27, 2017.

McKendry et al., "Pressure Waveforms to Assess Epidural Placement: Is There a Role on Delivery Suite?", Anaesthesia, 72, 2017, pp. 815-820.

NL Search Report, NL 2002708, dated Oct. 9, 2009.

(56) References Cited

OTHER PUBLICATIONS

Official Action issued in U.S. Appl. No. 11/208,400 on May 29, 2008 10 pages.
PCT International Prelminary Report on Patentability, PCT/NL2010/000061, dated Oct. 4, 2011.
PCT International Search Report, PCT/NL2010/000061, dated Aug. 23, 2010.
Product brochure "PAJUNK: NerveGuard Automatic system for injection pressure limitation" (XS200192B) dated Jan. 2017, 4 pages.
Ross et al., "Pressures of Injection in a Cadaver Model of Peripheral Nerve Blockade", Journal of Anesthesia & Clinical Research, 2014, vol. 5, Issue 10, 4 pages.
Suwa et al, "Pressure-Guided Method for Identification of the Epidural Space in Children", Anesthesiology, vol. 89, No. 2, Aug. 1998, pp. 546-548.
Tsui et al., "Reduced Injection Pressures Using a Compressed Air Injection . . . ", Regional Anesthesia and Pain Medicine, vol. 33, No. 2, Mar.-Apr. 2008, pp. 168-173.
Wagshul et al, "The pulsating brain: A review of experimental and clinical studies of intracranial pulsatility", http://www.fluidsbarrierscns.com/content/8/1/5, 2011, 8:5, 23 pages.
Lacoste, "DSSS in a nutshell The Powerof Patterns at Play", Circuit Cellar, Apr. 2020, #357, pp. 62-67.
International Search Report & Written Opinion issued in International Application No. PCT/US20/29857 on Jul. 21, 2020.

\* cited by examiner

DEVICE AND METHOD FOR NEEDLE/CATHETER LOCATION UTILIZING CORRELATION ANALYSIS

RELATED APPLICATIONS

This is a continuation of U.S. application Ser. No. 16/858,094, filed Apr. 24, 2020, now abdandoned, the entire contents of which application(s) are incorporated herein by reference.

FIELD OF THE INVENTION

The present invention relates generally to devices and methods for determining needle or catheter location in a patient utilizing a correlation analysis, and more particularly, but not exclusively, to correlation analysis, such as comparison of beats-per-minute or cross-correlation of waveforms, of objective pressure in the needle or catheter and the patient's heart rate pulse.

BACKGROUND OF THE INVENTION

Currently, when measuring pressure within a needle or catheter, there is no ability to identify false-positives of a cardiac pulsewave detected in the needle or catheter as opposed to pressure changes which truly represent the cardiac pulsewave. As used herein cardiac pulsewave is defined to mean a pressure waveform which contains a signal which originates from the contraction of the heart or vessels, and therefore contains information representing, the cardiac pulse. It is conceivable that a needle or an indwelling catheter can detect a non-cardiac pulsation from a variety of non-cardiac sources within the body, including respiratory changes, muscle movements of the diaphragm, etc, and can falsely report that detected pulsation as the cardiac pulsewave. It is also conceivable that patient bodily movements, such as postural changes in position of the patient, could produce pressure changes that are measured and are misinterpreted as originating from the cardiovascular system. In particular, existing devices do not include an independent means to verify that a particular pressure waveform is from the heart, and thus cannot rule out false positives in which the detected waveform has come from a source other than the cardiovascular system. At the same time, determining the location or the patency of a needle or catheter is of great interest to the clinician, such as for delivering of a drug to a patient. Hence, the ability to ensure that the pressure being sensed is not confused with other pressure changing waves produced in the body is of great interest if one is to rely on this information as indicative of needle or catheter placement, which, in turn, will impact patient outcome.

For example, in clinical use, after the placement of a needle or catheter it is common to deliver a dose of medication. Subsequent administrations through a needle or catheter can be compromised due to potential blockage of the needle or catheter, or by migration of a needle or catheter from the original position. Therefore, catheter assessments may be required including determining if a catheter is clogged, determining if the catheter is fully functional, and determining if the catheter has moved from the initial location. The inability to accurately differentiate a catheter's function leaves the clinician in a serious and sometime dangerous quandary: is the failure due to effectiveness of the drug, movement of the catheter, a clogged catheter from precipitate or a blood clot?

The data also show that between 10 to 25% of all catheters need to be replaced on patients because of catheter migration after placement. Clinicians have difficulty determining the reason for the failure of a catheter. Typically it takes to 20 to 30 minutes to evaluate catheter function and placement as the clinician waits for an observation to a therapeutic drug response, because currently this is the only means to evaluate catheter function. This adds additional risks and additional costs to healthcare systems, as a non-functional catheter can require life-threatening time to assess. Thus, the difficulties and potential risks of catheter placement and monitoring are serious challenges, and therefore a predictable manner to differentiate these conditions would be of great value to patients and clinicians.

Even so, existing devices developed to detect pulsatile waveforms can be expensive and complicated to use, requiring the use of an electro-mechanical motor to deliver the fluid to the patient. Such devices do not allow a clinician to observe an objective pressure generated while manually infusing a drug using a handheld syringe as is typically or preferably done. Existing systems are also not designed with inputs from multiple sources to separately compare and analyze both a heart-beat and pulsatile pressure waveform during use, and so do not provide two distinct physiologic sources of heart rate to determine and verify needle or catheter location. As such, the inventors, in arriving at the present invention, have recognized deficiencies in prior art devices and methods for needle or catheter placement, such as the ability to: 1) detect an input source of a cardiovascular system in which the heart-rate is used for direct comparison with needle or catheter location; 2) detect a cardiovascular response via a direct fluid path and analyze the information in the fluid path to produce beats-per-minute analyses to compare to a secondary source which is known to be detecting a heartbeat; 3) correlate and analyze more than one signal to determine that a needle or catheter is properly placed within an anatomic location; and 4) to provide a positive alert when these two signals are correlated within a range to confirm a true-positive.

Therefore, there is a need in the art for inexpensive and simple devices and methods that are capable of eliminating false-positives when locating a needle or catheter in the body which devices and methods would be of great value to the clinician and to the treatment of patients.

SUMMARY OF THE INVENTION

In view of the above-noted and other needs, in one of its aspects the present invention may provide devices and methods which use two or more different physiologic sources indicative of the cardiac pulse to determine needle or catheter placement prior to medication delivery or fluid aspiration. One of the sources may be the cardiac pulsewave detected as a pressure waveform in the needle or catheter, such as by an in-line pressure sensor, and a second source may be heartbeat detection from a finger pulse sensor, for example, or other location known to emit the cardiac pulsewave or heartbeat. The two physiologic sources may then be compared to verify that the pressure waveform detected in the needle or catheter is in fact the cardiac pulsewave, thus eliminating false-positive indications of the cardiac pulsewave in the needle or catheter. The comparison may be performed as a correlation analysis of signals from the two different physiologic sources to determine if the frequency of the signals from the two different physiologic sources is clinically comparable. The correlation analysis may be performed as a comparison of the numerical value of heart rate in beats-per-minute as detected at each of the two or more different physiological sources and/or by cross-correlation of waveforms detected at each of the two or more different physiological sources, for example. Thus, the present invention can perform "Needle/Catheter Location Correlation Analysis" as a comparison of two or more cardiovascular signals which may include beats-per-minute, cross-correlation of pressure waveforms, and/or objective pressure measurements, for example, to determine the location of a needle or a catheter within a mammalian body.

Positive verification of the cardiac pulsewave in the needle or catheter may establish both the correct position of the needle or catheter and its patency. As a result, devices and methods of the present invention can allow clinicians to more easily assess in real-time proper needle or catheter placement with confidence, due to the verified detection of the cardiac pulsewave. These may be presented to the clinician as a signal or an alert confirming proper needle or catheter placement. As a result, with the verified real-time detection of the cardiac pulsewave in the needle or catheter the clinician may use a manual syringe rather than an automated mechanical pump such that the clinician can personally position the needle and control the delivery of medication or aspiration of fluid and the accompanying physical force applied to the syringe. More precise control of the physical force by the clinician can also prevent catheter movement from excessive pressures. Excessive pressure during medication delivery could cause the dislodgement of the needle or catheter from a site as uncontrolled fluid pressures produce a "jet-stream" at the tip of the catheter or needle.

In another of its aspects, devices of the present invention may provide a clinician with an objective (i.e. measured) pressure value in the needle or catheter during the flushing stage. Knowing the objective pressure as a medication is injected can also assist the clinician in avoiding excessive force, preventing excessive pressures. For example, the present invention may alert the clinician when a pressure value has been exceeded. The alert can be audible, visual, haptic or the like.

Exemplary uses of devices and methods of the present invention may include locating a needle within the body to a specific target site, such as that of an epidural procedure or peripheral nerve block. In particular the identification of the epidural space, the determination of needle proximity to a neurovascular bundle in regional peripheral nerve blocks, and other medical procedures which require a needle or catheter tip to be positioned at a specific location (e.g., intrathecal, intravenous, intra-arterial, organ of the body) where the cardiac pulse is present, all can benefit from devices and methods of the present invention. Accordingly, the use of devices and methods of the present invention at such exemplary target sites can with greater reliability replace the current Loss-of-Resistance technique (LOR-technique). Further to its advantages, devices and methods of the present invention may be used for all types of needles and catheters that are placed into patients at anatomic sites at locations that emit a rhythmic pulsation of the arterial system, and may be provided as an inexpensive and portable system.

In still further of its aspects the present invention may achieve a number of objectives. For example, an objective of the invention may be to detect a pulsatile waveform of a catheter which is verified for the presence of a cardiovascular pulse by comparing a first input to a second input from the cardiovascular system, such as a heartbeat detected from a second input source. The redundant nature of these two sources may be identified and confirmed electronically and produce an alert to the operator. A further objective of the present invention may be to provide an inexpensive device to determine an objective pressure value that is generated when a drug is injected through a catheter using a manual syringe to prevent excessive pressure production at the tip of a catheter that might dislodge the catheter from a target position. Devices of the present invention can enable an audible alert to be set for a maximum pressure value to alert the operator if they have exceeded a specific pressure value. In addition, a further objective may be to detect and display a pulsatile pressure waveform corresponding to the pulse of the cardiac-vascular system to determine the position of a catheter. A further objective of the invention may be to provide a method and device that can detect the pulsatile pressure waveform that is present in the epidural space or intrathecal space of the central nervous system and detecting a pulsatile waveform or the proximity to the neurovascular bundle of nerve. A further objective may be to observe an objective pressure and graph an objective pressure value over time to monitor the response to an injection performed with a manual syringe to determine the patency of a catheter. Another objective may be to correlate an objective pressure value with a pulsatile pressure waveform to determine the patency and position of a catheter by simultaneously viewing the pressure/time graph and the pulsatile pressure waveform to determine catheter function. A further objective may be to provide a mean value of a pulsatile pressure waveform from an intravenous catheter to determine the patency of said catheter before, after and during an infusion.

In particular, in a first exemplary configuration, the present invention may provide an apparatus for confirming placement of a hollow-bore structure at a desired treatment location in a mammalian subject. The apparatus may include a first sensor operably connected to a lumen disposed in the hollow-bore structure; the first sensor may be configured to provide a first signal in response to detection of a first property indicative of a cardiac pulse in the lumen of the hollow-bore structure. The apparatus may include a second sensor configured to provide a second signal in response to detection of a second property indicative of the cardiac pulse. A controller may be operably connected (wirelessly or wired) to the first and second sensors to receive the first and second signals, and maybe configured to compare the first and second signals to provide a comparison result, whereby the comparison result provides an indication of placement of the hollow-bore structure relative to the desired treatment location. The first and/or second physical property may be one or more of a pressure, change in fluid volume, an electrical signal, and an optical signal. The first and second properties may relate to the same physical property or different physical properties indicative of the cardiac pulse. The hollow-bore structure may include one or more of a needle and a catheter. The first sensor may include an in-line pressure sensor having a sensor lumen disposed in fluid communication with the lumen of the hollow-bore structure, and the second sensor may be a finger pulse sensor. One or more of the first and second sensors may include a memory configured to store an indication that the first or second sensor, respectively, has been used. The device may also include an identification circuit embedded within or connected to one or more of the first and second sensors, wherein the identification circuit is configured to provide a signal to the controller, the signal including one or more of: a configuration signal indicative of physical characteristics of the first or second sensor; a verification signal indicative of the first or second sensor; and a use signal so that the controller can detect the number of times or length of time the first or second sensor was previously used.

In a second exemplary configuration the present invention may provide an apparatus for confirming placement of a hollow-bore structure at a desired treatment location in a mammalian subject having a controller configured to receive a first signal from a first detector placed at the treatment location. The first signal may be indicative of a cardiac pulse in the hollow-bore structure. The controller may also be configured to receive a second signal indicative of the cardiac pulse from a second detector placed at a second location. The controller may be programmed to compare the first and second signals to provide a comparison result, whereby the comparison result provides an indication of the placement of the hollow-bore structure relative to the desired treatment location.

For both the first and second (or other) exemplary configurations, the first and/or second signal may represent one or more of a pressure, change in fluid volume, an electrical signal, and an optical signal. The first signal may have a first period and the second signal may have a second period, and the controller may be configured to compare the first and second periods to provide the comparison result. (In addition, the first signal may include a waveform having a first period and the second signal may include a waveform having a second period, and the controller may be configured to compare the first and second periods to provide the comparison result.) Further, the first signal may include a first numeric value indicative of a frequency of the first signal, and the second signal may include a second numeric value indicative of a frequency of the second signal, and the controller may be configured to compare the first and second numeric values. One or more of the first and second numeric values may be a cardiac pulse in beats-per-minute. The controller may also be programmed to perform a cross-correlation analysis of the first and second signals. The controller may be configured to create an alert signal when the comparison result is within a selected value. In addition, a display may be operably connected to the controller for receiving one or more of the first and second signals and the comparison result from the controller. In one desirable configuration, the controller may include the display. The display may include a first data section for displaying a pressure detected by the first sensor in the lumen disposed in the hollow-bore structure, and may include a second data section for displaying the first and second signals. The first and second signals may each include a respective waveform, and the second data section may include a graph displaying the respective waveforms of the first and second signals. The display may also include a section for displaying an alert indication when the comparison result is within a selected value. The alert may be one or more of an auditory, visual, and haptic signal.

BRIEF DESCRIPTION OF THE DRAWINGS

The foregoing summary and the following detailed description of exemplary embodiments of the present invention may be further understood when read in conjunction with the appended drawings, in which.

DETAILED DESCRIPTION OF THE INVENTION

Figure 1:
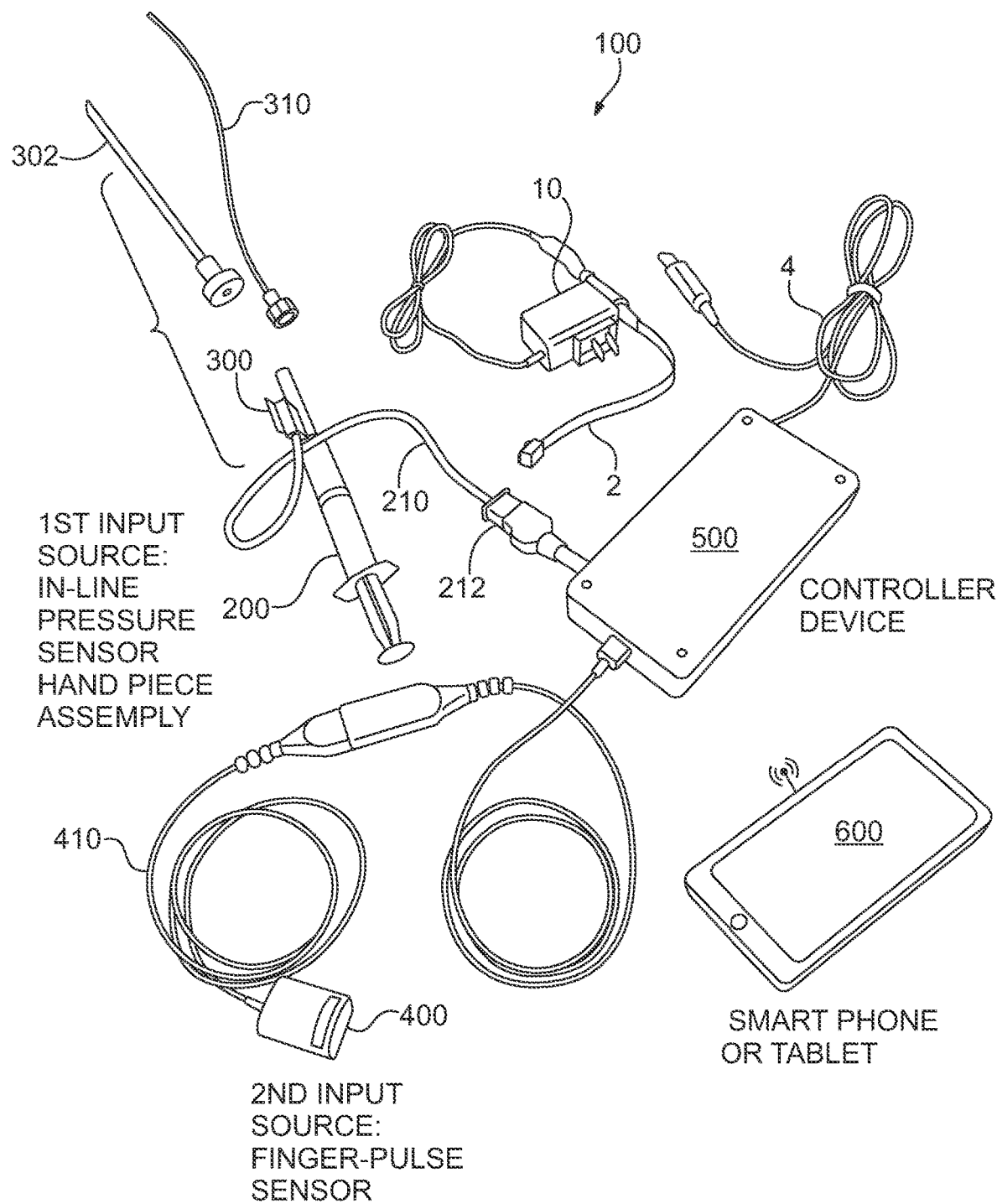
FIG. 1 schematically illustrates an exemplary configuration of a device for needle or catheter location in accordance with the present invention in which both a controller and display device are used.
Figure 2:
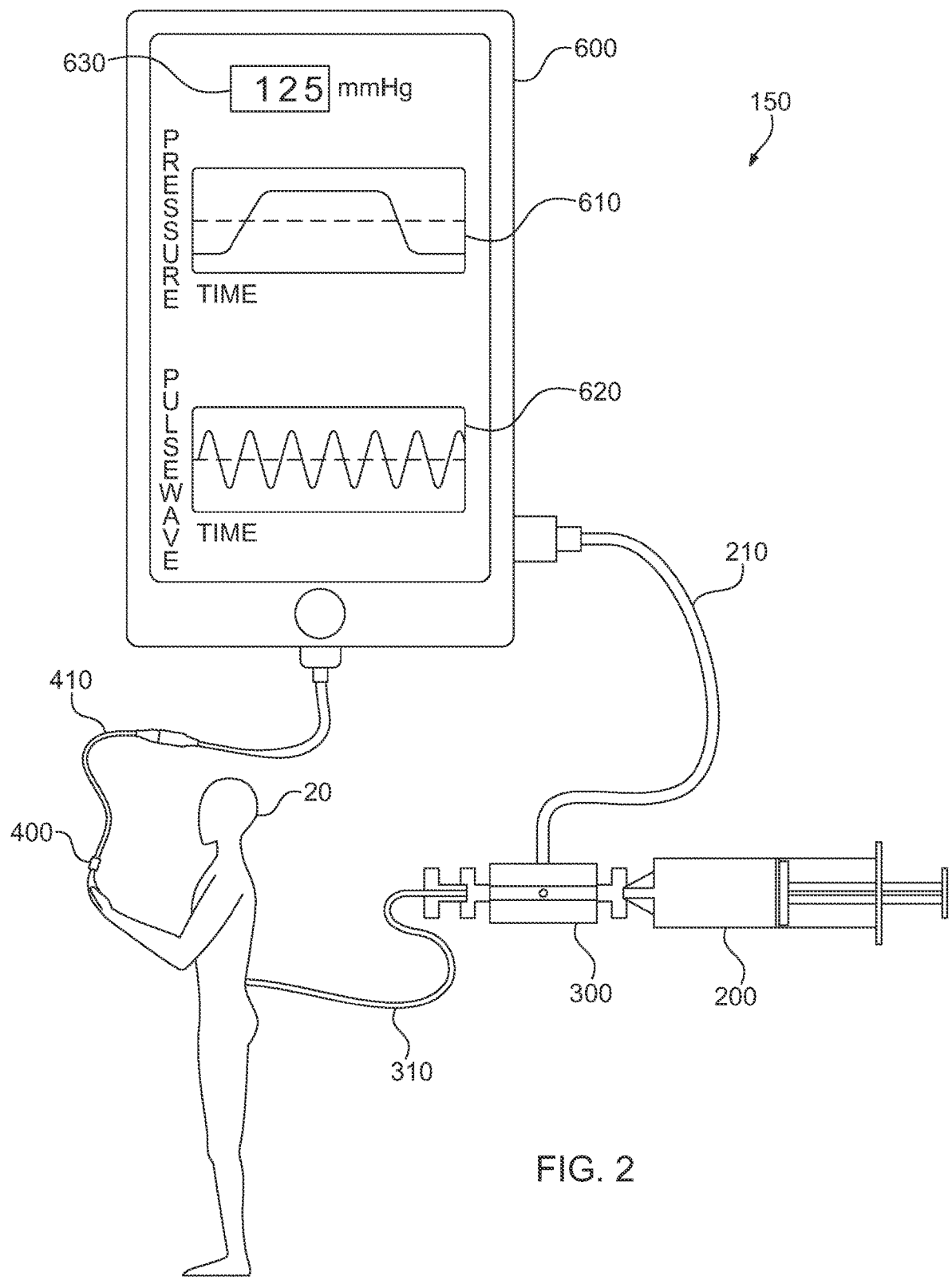
FIG. 2 schematically illustrates a further exemplary configuration of a device in accordance with the present invention in which a separate controller is not used.

Referring now to the figures, wherein like elements are numbered alike throughout, FIGS. 1, 2 schematically illustrate exemplary configurations of devices 100, 150 of the present invention for determining proper placement of a hollow-bore structure, such as a needle 302 and/or catheter 310, at a selected treatment location in a patient 20 using at least two independent measurements of the cardiac pulse, one of which measurements is detected via the hollow-bore structure. For example, the detection of the cardiac pulse via the needle 302 and/or catheter 310 may be accomplished by sensing a physical property in the lumen of the needle 302 and/or catheter 310, such as a physical property representing the pressure or fluid volume change in the lumen, where the variation in the pressure or fluid volume change contains a signal created by, and indicative of, the cardiac rhythmic contraction, e.g. the cardiac pulsewave. In particular, an in-line pressure sensor 300 may be provided in fluid communication with, and between, the needle 302 (or catheter 310) and a manual, handheld syringe 200, FIGS. 1, 2.

The second of the two independent measurements may be detected by a second device, such as a finger pulse sensor 400, disposed at a location on the patient 20 at which a physical property representing the cardiac pulse may be detected, FIG. 2. The physical property may be a pressure, an electrical signal, an optical signal, or other suitable signal, for example, that provides for independent verification of the presence of the cardiac pulse detected in the needle 302 and/or catheter 310. The physiologic location of the second device 400 may be different from that of the needle 302 and/or catheter 310.

Through the use of two independent measurement sources 300, 400 for the cardiac pulse, devices 100, 150 of the present invention can compare the signals from the two separate sources 300, 400 to confirm that the signal from the needle 302 and/or catheter 310 is indeed the cardiac pulse, which in turn will confirm that the needle 302 and/or catheter 310 is in the "correct" location for procedures in which the target tissue is one in which the cardiac pulse is expected to be present. For example, target sites for correct needle or catheter placement in which the cardiac pulse is expected to be present include the epidural space, intrathecal space, or proximate to a neurovascular bundle or other anatomic structure that emits a pulsatile wave produced by the cardiovascular system, including the heart itself.

Once confirmation of needle or catheter placement is confirmed by the device 100, 150, an alert may be provided to the clinician, and the clinician may proceed with injection or aspiration through the syringe 200, depending on the nature of the procedure being performed. The alert may be provided in any suitable form, such as auditory, visual, or haptic, for example. Thus, devices of the present invention are capable of location guidance and confirmation during the placement of a needle 302 and/or catheter 310. Indeed, devices and methods of the present invention may confirm patency of the needle 302 and/or catheter 310.

Turning to FIG. 1 in more detail, operation of the sensors 300, 400 may be provided by a dedicated controller device 500. The controller device 500 may be operably connected to the sensors 300, 400 via respective cables 210, 410, and in certain cases an adapter 212 may be provided between the controller device 500 and a respective cable 210. Alternatively, the sensors 300, 400 may communicate wirelessly with the controller device 500, via any suitable communications technology such as Bluetooth® communication. The sensor 300 disposed in sensing communication with the needle 302 and/or catheter 310 may, as described above, be an in-line pressure sensor whose fluid path is continuous with the needle 302 and/or catheter 310, such as a Merit Medical, MER200. In such a case, the contraction of the heart produces propagation of an energy wave representative of the cardiac pulse into a fluid in the sensor 300 and the wave may be measured through pressure or volumetric changes therein. The changes may produce a repetitive signal in the form of a pulsewave signal and may be measured from peak-to-peak or zero crossings to determine the frequency of the pulsewave signal to yield the cardiac pulse rate in beats-per-minute. Alternatively, the sensor 300 could be positioned alongside the catheter 310 and/or could be interposed between an external fluid source such as an IV bag, syringe or any vessel that provides a continuous fluid line.

In addition, the sensor 300 (and/or sensor 400) may be one or more of an acoustic sensor, optical sensor, infrared detector or other device which detects the cardiac pulse which has propagated within tissues from the cardiovascular system to the location of the sensor 300, 400. In short, any sensor type capable of detecting the cardiac pulse in the lumen of the needle 302 and/or catheter 310, whether by pressure, sound, or other physical property, may be used as the sensor 300. Similarly, any sensor type capable of detecting the cardiac pulse at a physiologic source independent of the lumen of the needle 302 and/or catheter 310 may be used as the sensor 400 including one based on photophelthysmography (PPG) such as a Model 3231 USB or Model 3230 Bluetooth® Low Energy from Nonin® Medical, Inc, for example. Alternatively, the sensor 400 may be provided as a pneumatic inflatable cuff (such as that found in a sphygmomanometer). With a preference for using non-invasive methods for detecting the heart beat or beats-per-minute of the peripheral vascular system, it is also possible that the detection of the heart beat could be from an electronic signal that is captured with a heart-rate monitor in contact with the skin of a patient.

One or more of the sensors 300, 400 may also be provided in the form of a single use sensor which may be particularly desirable in the case where the sensors 300, 400 come in direct contact with bodily tissues or fluids, e.g. blood, cerebrospinal fluid, or fluid filled epidural space. For example, the sensor 300 may include a separate body fluid pressure sensor 305 and a microchip in the form of a programmable memory 320, FIG. 3, where the programmable memory 320 may be used to track usage of the sensor 300 and thereby limit the sensor 300 to a single use. Information communicated with the sensor 300 and memory 320 may be encrypted and coded to ensure security of the use of the sensor 300. Alternatively or additionally, sensor 300 can have an internal on-chip timer that allows a specified amount of time for use of the sensor, after which the sensor 300 expires. These features mitigate the potential for use on multiple patients and help to control against counterfeit products. The sensor 400 may be similarly configured for single use.

The data collected from the sensors 300, 400 may be transmitted to the controller device 500 for further processing, after which the processed data may be transmitted via a cable 4 or wirelessly to a display device 600, such as a computer, smart phone, tablet, or other handheld device, for viewing by the clinician, FIG. 1. The controller device 500 may include a circuit board, central processor unit, rechargeable battery, connectors for wired communication, and/or antennas for wireless communication via Wi-Fi, Bluetooth® or other suitable communications standard. The controller device 500 may both process the received data and control and provide power to the sensors 300, 400. The display device 600 may also further process the data prior to display and may include a variety of input elements such as buttons, a touchscreen, voice activated commands, scanning, etc. to transfer information into the controller device 500. Alternatively, the display device 600 may receive the data directly from the sensors 300, 400 and control the operation of the sensors 300, 400 so that a separate controller device 500 is not required, FIG. 2. In this regard, the display device 600 may include a software application that can collect, process and display input data received from the two or more separate input sources 300, 400 with or without use of the controller device 500. The data to be displayed by the display device 600 may include, but is not limited to, an objective pressure value 630, a graph of objective pressure over time 610, and a pulsatile waveform 620 representative of the contractive nature of the heart or cardiovascular system, FIG. 2. A prototype of the device controller 500 was constructed for use in the system 100 of FIG. 1.

Prototype Controller Circuit

Figure 3:
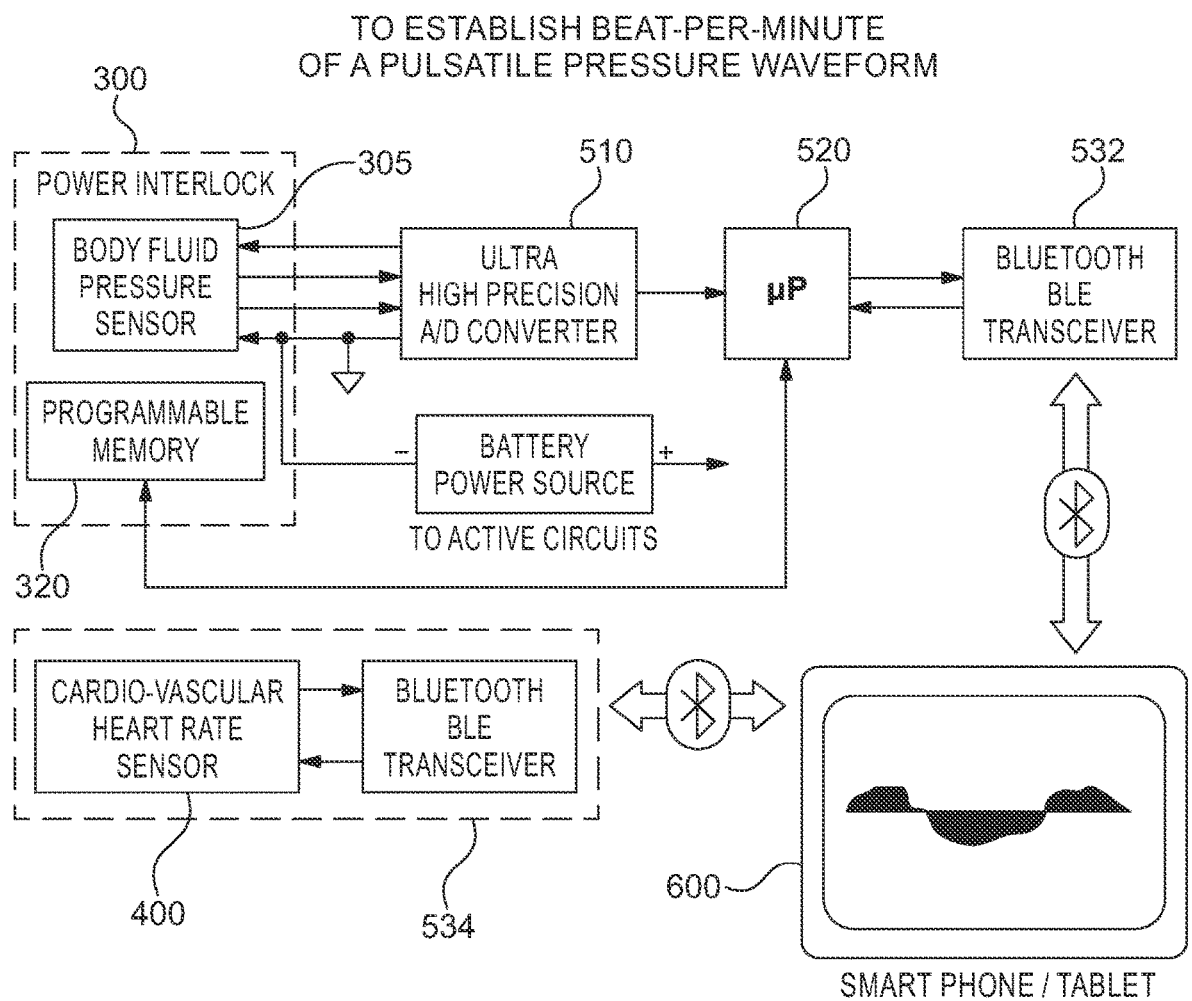
FIG. 3 schematically illustrates additional aspects of the devices of FIGS. 1 and 2.
Figure 6:
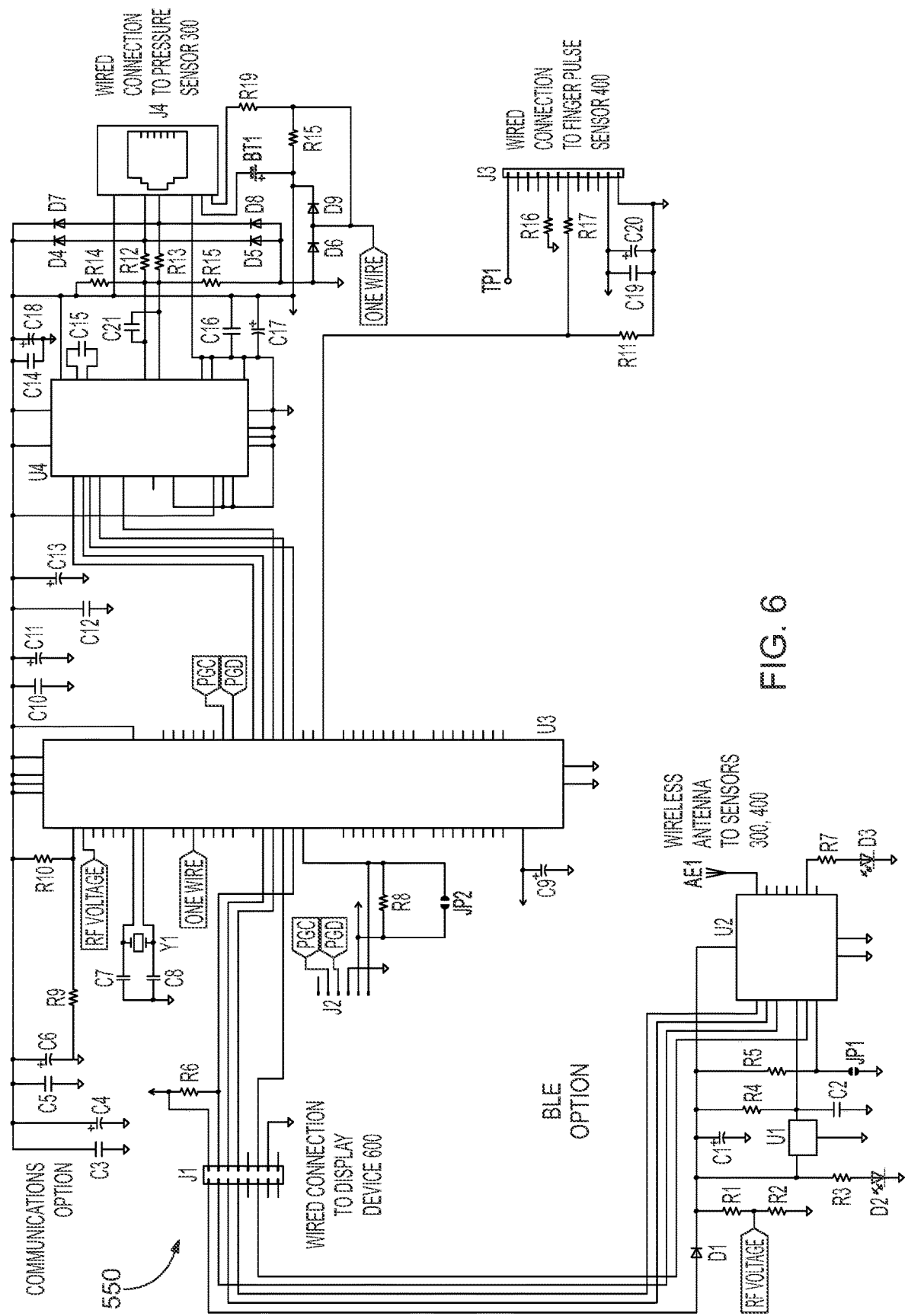
FIG. 6 illustrates a circuit diagram of an exemplary configuration of the controller of FIG. 1.

FIG. 6 illustrates a schematic of the circuit 550 used in the prototype controller 500 of FIG. 1. (The circuit 550 also represents at the component-level implementation of block diagram elements shown in FIG. 3. Reference to corresponding elements of FIG. 3 are provided parenthetically.) As shown in FIG. 6, two different communication options were provided, and both were tested: wireless communications via Bluetooth® transceiver U2 (e.g., transceivers 532, 534, FIG. 3), and direct wire communications via the USB serial data cables 210, 410, FIG. 1, connected to connector J1, FIG. 6. (Specifications for all components of the circuit 550 are provided in Table 1 below.) The prototype 100 collected data from the two sensors 300, 400 and provided the data to the controller 500 where the data were formatted for presentation to a user.

In the prototype 100, a Nonin Medical, Inc Xpod® 3012LP External OEM Pulse Oximeter with 8000A Reusable Finger Clip pulse oximetry sensor was used for the finger pulse sensor 400. The finger pulse sensor 400 produced a continuous stream of serial data which were input on connector J3. The data from the finger pulse sensor 400 were provided to the unit serial input receiver channel 1 at pin 38 of a microprocessor U3 (e.g., microprocessor 520, FIG. 3). A standard baud rate transmission was used which was set by resistor R16. The data were collected and assembled into a format simplified for use by the display device 600.

The in-line pressure sensor 300 was a piezoresistive bridge design Model MER200 from Merit Medical, Inc and was attached to connector J4, FIG. 6. The reference voltage used to power the in-line pressure sensor 300 was provided directly from the lithium-ion battery BT1 in the circuit 550. The in-line pressure sensor 300 was connected through an adapter 212, FIG. 1. The adapter 212 had several functions: to easily connect the sensor 300 to the controller 500 through an RJ12 quick connection connector J12; to provide power turn-on by interlock connection to the battery BT1; and, to permit identification and use management of the in-line pressure sensor 300 by a one-wire memory device.

A memory device 320 may be present in the in-line pressure sensor 300, FIG. 3, to identify and serialize the in-line pressure sensor 300 allowing traceable data to be collected and stored by the display device 600. In the prototype such a memory device was in the adapter 212. Use of the memory device 320 could also help mitigate the potential for use of the pressure sensor 300 on multiple patients. The sensor 300 and adapter 212, FIG. 1, may be disposable components intended for single use on one patient.

Since the device 100 had a user accessible connector J4, the circuit 550 included a protection against Electro-Static Discharge (ESD) events which could be caused by the accumulation of excessive static charge. Diodes D4-D9 were used to clamp the inputs of connector J4 to protect the internal circuitry, FIG. 6. The adapter 212 internally jumpered together pins 4 to 5 at connector J4, FIG. 6, which provided a connection path from the internal battery BT1 negative terminal to the remainder of the components of circuit 550. Thus, the circuit 550 was powered on when the adapter 212 was attached to the connector J4, which also helped mitigate exposure leakage current to users and patient when no adapter was present. Connector J4 was also used to charge the battery BT1 using an external charger 10 attached to J4 via cable 2, FIG. 1. The circuit 550 was not powered when the charger 10 was attached; only the battery BT1 was charged. The charge current was limited and monitored to provide protection against battery fault/fire protection.

As shown in FIG. 6, the signal from the in-line pressure sensor 300 was presented to chip U4, a high resolution 24-Bit analog-to-digital converter, (e.g., A/D converter 510, FIG. 3). The analog-to-digital converter U4 used, for its reference voltages, the same battery/ground voltage that powered the in-line pressure sensor 300. Hence, the analog-to-digital converter U4 made a ratiometric measurement of the signal from the in-line pressure sensor 300, and no correction was needed for gain and offset. The raw output of the analog-to-digital converter U4 was multiplied by a constant that was determined by the gain of the Merit MER200, which was pre-calibrated and adjusted during manufacturing. Resistors R14 and R15 of the circuit 550 provided mitigation for possible broken sensor leads for the in-line pressure sensor 300. In the event of a breakage, the pressure reading from the analog-to-digital converter U4 was driven to an upper or lower extreme and thus became invalid.

The data from the analog-to-digital converter U4 were sent to the microprocessor U3 over a serial peripheral interface (SPI) serial channel. The data from the analog-to-digital converter U4 were assembled in 3 bytes which were re-assembled in the microprocessor U3 as a 32-Bit word representing the catheter 310/needle pressure.

The microprocessor U3 maintained some data in non-volatile memory which included a device serial number, catheter gain correction, and general hardware settings. This data could be transferred to and changed by commands sent from the display device 600. This information was stored in EEPROM memory internal to the microprocessor U3.

While gathering the in-line pressure sensor data from the analog-to-digital converter U4, the microprocessor U3 also attempted to measure the cardio-induced pulse rate, if present, in the waveform signal from the in-line pressure sensor 300. An average value was calculated for the waveform signal and subtracted from the raw data to provide a zero-centered waveform. The zero-centered waveform was processed to identify zero-crossings in the zero-centered waveform from which the period of the peaks and valleys was determined. A measurement of the period from the peaks/valleys was made and converted into a beats-per-minute numeric value. The numeric value and the positive zero-crossing information was passed via a communication channel to the display device 600. Additional details on the operation of microprocessor U3 are discussed below in connection with FIG. 8.

As shown in FIG. 6, crystal Y1 was the clock source for microprocessor U3. The internal timing measurements and communication rate were established from this frequency choice. The frequency was chosen to provide sufficient computational speed while reducing radiated emission from the circuit 550. The 3.7 volt battery BT1 voltage also helped mitigate emissions. Voltage dividers consisting of R1/R2 and R9/R10 scaled the voltage from battery BT1 and radio transceiver U2 to a value in the range of the analog-to-digital converter internal to microprocessor U3 and allowed measurement of the supply voltages. This design was capable of operating with battery voltages below 3.0 volts. Over 12 hours of continuous operation was possible before battery recharging was required.

The microprocessor U3 was programmed in-circuit by attaching a standard Microchip Technologies programmer to J2. The code could be changed in-the-field as the software design included a boot-loader section. After first programming, a production jumper JP2 may have a solder connection placed across it to protect the circuit 550 from future programming. The jumper JP2 also improves protection against ESD events.

The circuit 550 included two options for communication with the display device 600. When the USB cable option was used, a Future Technologies Digital International (FTDI) serial-to-USB cable 4, FIG. 1, was connected to jumper J1 on the "b"-side, i.e., pins b2-b7. This provided direct attachment of the cable 4 to serial channel 2 of the microprocessor U3. The USB cable option was configured as a full implementation of RS-232 (TTL) using flow control CTS/RTS. The Smart USB cable 4 was powered by the display device 600 to which the USB connection was made. Power was not provided through the circuit 550. At the display device 600, the USB port was configured as a virtual communications serial port.

For wireless Bluetooth® communication, the FTDI cable 4 was removed and jumpers were placed across pins 3-8, a-to-b of jumper J1. The choice of communication baud rate was selected based on the default configuration of Bluetooth® transceiver, U3. The same baud rate was used for the FTDI USB cable. This allowed the microprocessor U3 to operate without regard to whether the information and commands were transferred from the display device 600 via USB or Bluetooth® communications.

The radio transceiver module U2 was a microchip design that simulated serial communication to the display device 600 and was pre-certified to meet the requirements of the FCC and EU standards for RF performance. The Green LED D2 indicated the radio transceiver module U2 was powered while the Red LED D3 flashed during data transmission, FIG. 6. The mode jumper JP1 was normally shorted and was used only for debugging purposes. Supervisory circuit U1 provided power-on and low-voltage shutdown of the radio transceiver module U2. The display device 600 was responsible for pairing and bonding to the transceiver antenna AE1 of the radio transceiver module U2. Operation of the transceiver U2 occurred according to the frequencies and protocols defined for Bluetooth® BLE. The radio transceiver module U2 was defined as a server device providing data to a slave. The radio transceiver module U2 wirelessly communicated with the display device 600, in the case of the prototype a tablet (Dell® Latitude 7200, 2-in-1 tablet), which executed the software for analyzing and displaying the signals from the two sensors 300, 400.

TABLE 1

Parts list for components shown in FIG. 6.

| Reference(s) | Part Number | Value | Description | Manf. |
|---|---|---|---|---|
| AE1 | — | Antenna | PWB trace Antenna | — |
| BT1 | LP503562JB | Lithium Ion Battery | Battery Lithium Polymer 1S1P 1250 MAH 3.7 VBATT LITH POLY 1S1P 1250 MAH 3.7 V | Jauch Quartz |
| C1, C4, C6, C9, C11, C13, C17, C18, C20 | ECA-1EM100B | 10 uf | Capacitor, Aluminum, 10UF 20% 25 V RADIAL | Panasonic Electronic Components |
| C2, C3, C5, C10, C12, C14, C15, C16, C19, C21 | C320C104K5R5TA7303 | 0.1 uf | Capacitor, Ceramic, 0.1 uf, 50 v, X7R Radial | Kemet |
| C7, C8 | C315C220K2G5TA | 22 pf | Capacitor Ceramic, 22PF 10% 200 V C0G RADIAL | Kemet |
| D1, D4, D5, D6, D7, D8, D9 | 1N4148 | 1N4148 | Diode, General Purpose, 100 V 200 MA DO35 | ON Semiconductor |
| D2 | HLMP-CM1G-350DD | Green | LED GREEN CLEAR T-1 3/4 T/H | Broadcom Limited |
| D3 | HLMP-1700-B0002 | Red | LED RED DIFFUSED T-1 T/H | Broadcom Limited |
| J1 | 67996-416HLF | Communications Option | Connector, Header, Vert, 16POS 2.54 MM | Amphenol ICC(FCI) |
| J2 | 68000-406HLF | Progrm. Conn. | Connector, Header, Vert, 6POS 2.54 MM | Amphenol ICC(FCI) |
| J3 | LX60-12S | Xpod Connector | Connector Receptacle 12P 0.02 GOLD SMD R/A | Hirose Electric Co Ltd |
| J4 | 0950097667 | ID Adapter Conn. | Connector, CONN MOD JACK 6P6C R/A UNSHLD | Molex |
| JP1 | — | Mode Jumper | Solder Jumper, PWB trace | — |
| JP2 | — | Production Jumper | Solder Jumper, PWB trace | — |
| R1, R2, R8, R9, R10 | CFR-25JB-52-47K | 47.0K | Resistor 47 KOhm 1/4 W 5% Axial | Yageo |
| R3, R7 | CFR-25JB-52-470R | 470 | Resistor 470 Ohm 1/4 W 5% Axial | Yageo |
| R4, R6, R17 | CFR-25JB-52-10K | 10.0K | Resistor 10 KOhm 1/4 W 5% Axial | Yageo |
| R5 | CFR-25JB-52-100K | 100K | Resistor 100 KOhm 1/4 W 5% Axial | Yageo |
| R11 | CFR-25JB-52-68K | 68K | Resistor 68 KOhm 1/4 W 5% Axial | Yageo |
| R12, R13 | CFR-25JB-52-1K | 1.0K | Resistor 1.0 KOhm 1/4 W 5% Axial | Yageo |
| R14, R15 | CFR-25JB-52-10M | 10M | Resistor 10 MOhm 1/4 W 5% Axial | Yageo |
| R16 | CFR-25JB-52-4K3 | 4.3K | Resistor 4.3 KOhm 1/4 W 5% Axial | Yageo |
| R18 | CFR-25JB-52-2K2 | 2.2K | Resistor 2.2 KOhm 1/4 W 5% Axial | Yageo |
| R19 | CFR-25JB-52-10R | 10 | Resistor 10 Ohm 1/4 W 5% Axial | Yageo |
| U1 | MCP112T-270E/MB | MCP112T | IC SUPERVISOR 1 CHANNEL SOT89-3 | Microchip Technology |
| U2 | RN4871-I/RM130 | RN4871 | Bluetooth ® BLE Module, shielded | Microchip Technology |
| U3 | PIC18F87K22-I/PT | PIC18F87K22-xPT | IC MCU 8 BIT 128 KB FLASH 80TQFP | Microchip Technology |

TABLE 1-continued

Paits list for components shown in FIG. 6.

| Reference(s) | Part Number | Value | Description | Manf. |
|---|---|---|---|---|
| U4 | ADS1232IPWR | ADS1232 | IC ADC 24 BIT SIGMA-DELTA 24TSSOP | Texas Instruments |
| Y1 | ECS-160-S-5PX-TR | 16 MHz | Crystal Oscillator, 16.0 MHz, series resonant | ECS Inc. |

Display Device

Figure 4:
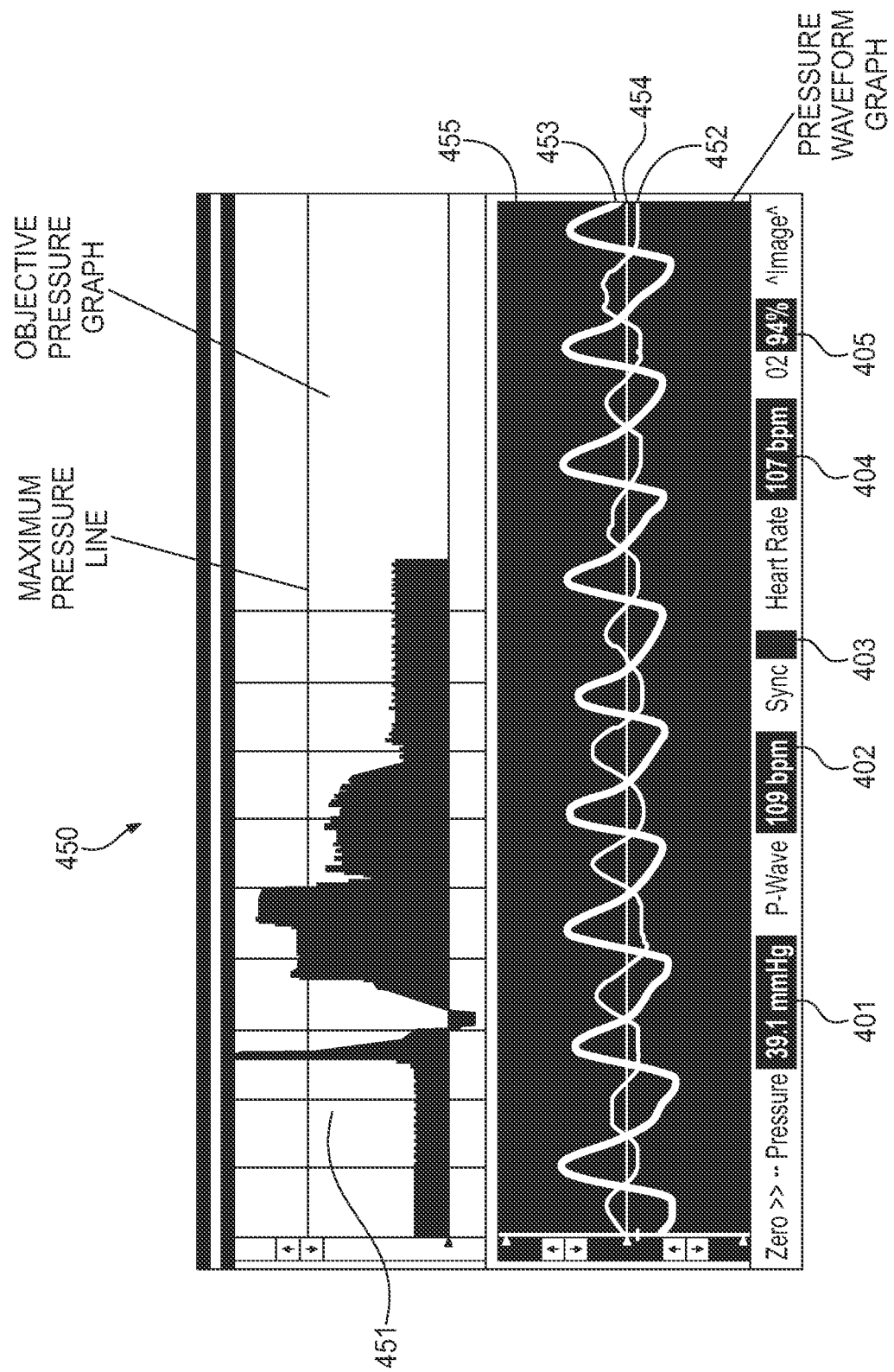
FIG. 4 schematically illustrates an exemplary configuration of a display of a prototype in accordance with FIG. 1 of the present invention, in which the display shows objective pressure over time and cardiac pulsewaves and pulse detected from two independent sources, along with numerical display in real-time of clinically useful parameters of objective pressure and the numerical pulse rates of each of the two independent sources, along with an indicator showing whether or not the two independent sources are correlated in frequency (i.e., that the two independent sources both relate to the cardiac pulse)

Turning to the display device 600 and signal analysis in more detail, the display device 600, working alone or in concert with the controller device 500, may produce useful data and alerts to the clinician to aid in the placement of the needle 302 and/or catheter 310, including providing an indication of patency of the catheter 310, FIGS. 2, 4. FIG. 4 schematically illustrates an actual screenshot provided on the display device 600 as used with the working prototype 100 of FIG. 1, which included the controller device 500 with controller circuit 550. FIG. 4 provides but one exemplary output configuration for data in accordance with the present invention.

With reference to FIG. 4, a display 450 on an LCD screen of the display device 600 included two graphs. The upper half of the screen displayed an "Objective Pressure Graph" 451 and in the lower half displayed a "Pressure Waveform Graph," 455 showing waveforms 452, 453 corresponding to data collected from the sensors 300, 400, respectively. In addition, a Dialogue Bar was provided below the Pressure Waveform Graph. These two graphs can be shown simultaneously or can be displayed individually at different times.

The objective pressure was displayed in both the Objective Pressure Graph showing a scrolling graph of objective pressure vs. time 451 and as a real-time numeric value 401, FIG. 4. A Maximum Pressure Line was also displayed, which could be changed by the clinician. When the objective pressure exceeded this line, an audible alert was sounded, though it is understood that the audible alert could have been a visual or some other type of alert. The objective pressure 401 corresponded to pressure generated by the handheld syringe 200 as the clinician applied a force to the plunger of the syringe 200. The graphing of the objective pressure data was performed on a continuous basis and in real-time, and the scaling could be changed by pressing the Up and Down arrows (↑, ↓) on the left-hand side bar of the Objective Pressure Graph 451, which allowed scaling to be changed in real-time. If the pressure detected reached the Maximum Pressure Line without the expression of fluid, the clinician could conclude that the needle 302 and/or catheter 310 is occluded. A negative slope in the Objective Pressure Graph could indicate a dissipation of the pressure in the needle 302 and/or catheter 310, further indicating that the needle 302 and/or catheter 310 was not occluded. Thus, the real-time changes in the Objective Pressure Graph provide vital information to confirm or rule out an occluded needle 302 or catheter 310 even when the data from the waveforms 452, 453 are ambiguous. Therefore, the Objective Pressure Graph provides needle or catheter patency information in addition to the information displayed in waveforms 452, 453.

As to the Pressure Waveform Graph 455, the waveforms 452, 453 were constructed using a high resolution, high-speed sampling algorithm in which between 30 to 90 samplings per second were taken. In the prototype, average values of the waveforms 452, 453 were calculated and drawn to the display device 600 to maintain the waveforms 452, 453 centered on the Pressure Waveform Graph. Within 4 seconds (or some other programmed period of time in the software), the displayed waveform 452, 453 was calculated to a mean pressure value and positioned to be centered within the graph 455 relative to the mean horizontal line 454 displayed in FIG. 4.

The waveforms 452, 453 from the first and second sensors 300, 400 had peak-to-peak crests (and zero crossings) that were reflective of the pulsatile nature of the heart contracting and were consistent with the value of the number of heart beats-per-minute (bpm). The heart rate in beats-per-minute could also be calculated from the zero crossings. However, two zero-crossings are present per beat, so either time between successive positive-slope zero crossings or time between successive negative-slope zero crossings were indicative of heart rate. The two waveforms 452, 453 could be visually compared on the display 450 by the clinician. In addition, a real-time numerical value 402 for the heart rate detected by the first sensor 300 was displayed, as well as the real-time numerical value 404 for the heart rate detected by the second sensor 400, FIG. 4. The detection of a both waveforms 452, 453 from the two input sources 300, 400 provides the clinician with an understanding as to the position of the needle 302 and/or catheter 310 within an anatomic structure that transmits a pulse wave from the cardiovascular system. Two sets of up and down arrows (↑, ↓) on the left-hand side bar of the Pressure Waveform Graph were usable to scale the heights of each of the waveforms 452, 453 individually. In addition, an audible bpm beep could be provided which sounds with the same frequency as the pulse rate shown in either waveform 452 or waveform 453. In such a case display of the waveforms 452, 453 associated with the audible bpm beep could be omitted, with the audible bpm beep filling the role of providing such information to the clinician.

Alternatively, the waveforms 452, 453 could be displayed in a variety of different formats. Exemplary formats may include, (and are not limited to): a continuous waveform which may be represented as a pressure waveform with peak-to-trough continuous line; a non-continuous line in which the peak-to-peak is displayed; or, a blinking light that is representative of the peak-to-peak pressure values that are detected by the input sources. In addition, it may be that the waveforms 452, 453 are not both displayed but only a visual alert is provided confirming that the signals are coordinated with the peak-to-peak signal representative of heart beats-per-minutes from the two independent sources 300, 400. For instance it is possible that neither of the waveforms 452, 453 are displayed, and that the peak-to-peak signals are represented as an audible or haptic signal. Or it is possible to rely solely upon the numeric values displayed as beats-per-minute. Further, any combination of these display techniques may be used.

As shown in FIG. 4 the Dialogue Bar included (from left to right): 1) a "Zero" button to calibrate the in-line pressure sensor 300; 2) an objective pressure value 401 for the in-line pressure sensor 300; 3) heart rate beats-per-minute (bpm), 402 from the in-line pressure sensor 300; 4) a "Sync alert" 403 indicating that the heart rate values 402, 404 were correlated to confirm that a single source (the heart) has produced both of these signals; 5) a heart rate beats-per-minute (bpm) 404 from the finger pulse sensor 400; 6) an oxygen saturation value 405 in percent; and 7) an "^image^" button to capture the image on the screen.

The display device 600 in the prototype performed an analysis to determine whether the two waveforms 452, 453 were correlated at their fundamental frequency, which frequency corresponded to the cardiac bpm (beats-per-minute) if the waveform 452, 453 represented the cardiac pulsewave. If not, the fundamental frequency would correspond to some other spurious signal not related to the cardiovascular system. Two signals were considered correlated in frequency even if a phase offset between the two signals were present, such as illustrated in the waveforms 452, 453, FIG. 4. A phase offset between the signals may be present due to the fact that the cardiac pulse may travel through different tissue types and different distances to arrive at each of the sensors 300, 400.

If the waveforms 452, 453 were frequency-correlated, the "Sync alert" 403 would flash on/off to alert the clinician that the bpm rates from each of the sensors 300, 400 were found to be correlated, i.e., that the frequency of signals from the sensors 300, 400 were sufficiently matched within a selected deviation, with an acceptable range of deviation of 2 bpm to 15 bpm. Thus, the clinician was provided with a confirmation of location of the needle 302/catheter 310 at the desired location when the "Sync alert" 403 was activated. In addition, an alert may optionally be sounded if the two waveforms 452, 453 were not correlated, indicating that the needle 302 and/or the catheter 310 was not positioned properly. Any of these alerts may be visual, audible, haptic, or any combination thereof.

The signals detected by the sensors 300, 400 may also be analyzed by a variety of correlation techniques to determine the cardiac pulse rate, including but not limited to, waveform analysis, pulse-rate comparison (heart-rate, beats-per-minute), cross-correlation, and combinations thereof. In yet another embodiment a cross-correlation analysis may be performed on the data from the sensors 300, 400 producing a matched frequency of the two signals with time-shift producing definitive positive correlation based on set a criteria. In this case, the cross-correlation may be the sum of the product of the two signals shifted relative to each other over a period of not less than one complete cycle of the longer period waveform. In yet another embodiment auto-correlation may be used to normalize the values for better threshold detection comparison of the cross-correlation peak value. In yet another embodiment the auto-correlation peak spacing can be used to verify the validity of the BPM measurements made of each sensor data.

Figure 9:
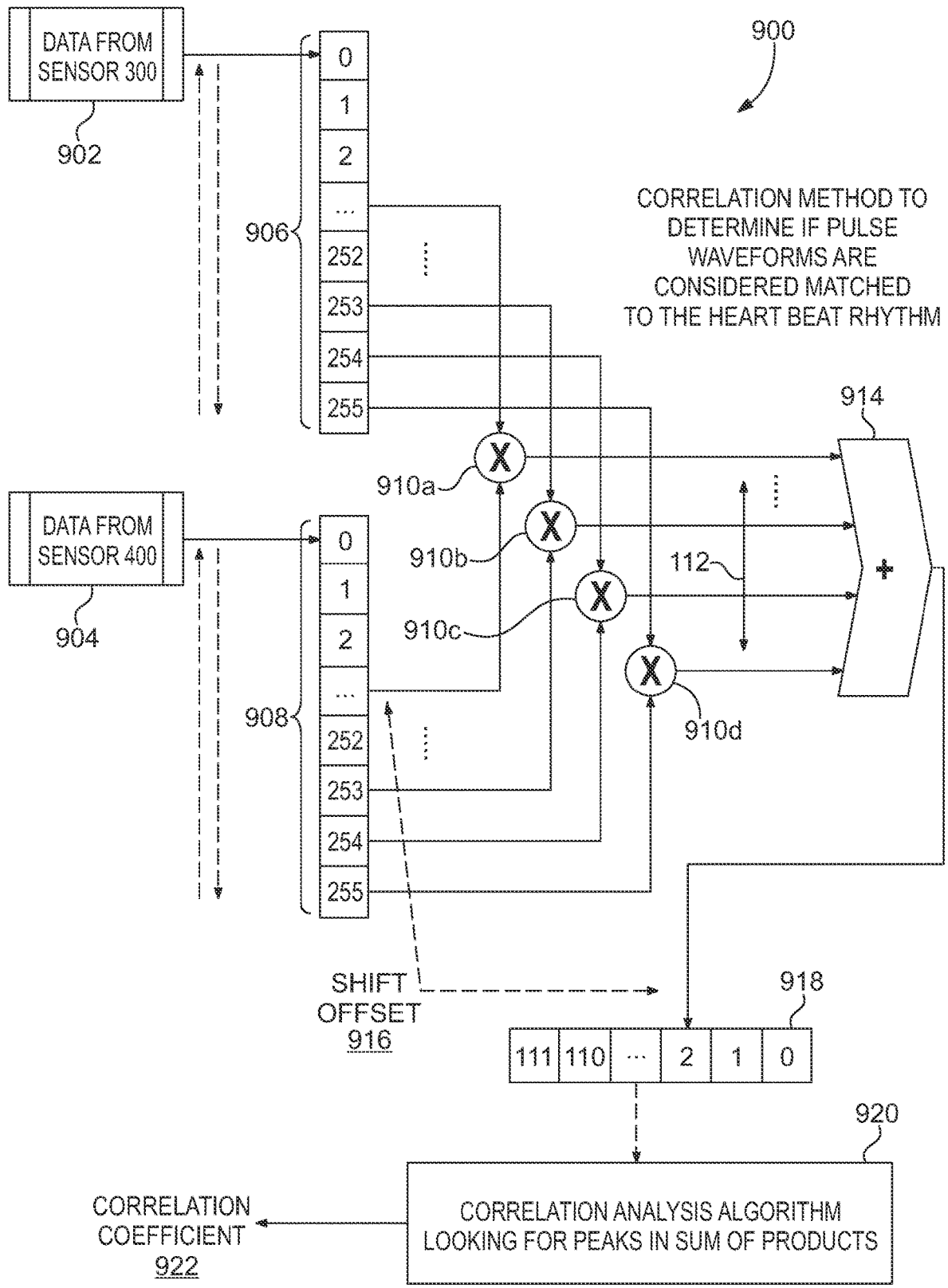
FIG. 9 illustrates a further method for performing signal correlation in accordance with the present invention.

In yet another embodiment a cross-correlation analysis may be performed on the data from the two input sources 300, 400 producing a definitive positive correlation based on set criteria. Illustrated in FIG. 9 is an example of a cross-correlation technique in accordance with the present invention that may be used to objectively determine the degree of correlation of the two signals 452, 453 from sensors 300, 400. Exemplary details are specific to an implementation for the controllers 500 and 600. For discrete data samples as collected by exemplary devices 100, 150 of the present invention, the cross-correlation function may be defined as $$(f*g)(\tau) \triangleq \sum_{t0}^{t0+T} \overline{f(t-\tau)} g(t) dt,$$

where T is the period (number of samples) of the waveform being analyzed, and $\tau$ is the sliding offset between the two waveforms.

Basically, the correlation function generates a series of sum-of-products over the entire sampled data set to come up with values of the correlation coefficient for each T value. The correlation coefficients calculated have a maximum value at shift $\tau_{max}$. Due to possible velocity propagation delays through the patient tissue, the two waveforms 452, 453 may have an offset in the peak correlation coefficient position, in which is $\tau_{max} \neq 0$. The method 900 shown in FIG. 9 presents a representation of an exemplary method which may be used for correlation detection in accordance with the present invention. The collected data from the in-line pressure sensor 300 is input at step 902. The pressure reading from the finger-sensor 400 is input at step 904. The data are collected synchronously by display device 600, and hence the pair of data (902, 904) represents a single instance in time. The sampled data are placed in circular FIFO buffers 906, 908. The size of the buffers 906, 908 is determined by the period of the pulsewaves 452, 453. The longest period occurs at the lowest pulse rate which is defined to be 40 BPM. With a data sampling frequency of 75 samples/second, a minimum of 112 samples represent one complete wave form in each buffer 906, 908. In addition, the $\tau$ shift could be up to 112 samples as well. Hence, the minimum buffer size to perform a complete cross-correlation function is 224 for the combined buffers 906, 908. In this exemplary case, the buffer length may be chosen as 256, which makes circular FIFO buffer management easier and also provides some addition space in the buffers 906, 908. An extra 32 buffer positions of padding (256−224=32) may be provided that allow new data to be inserted into the circular buffers 906, 908 without corrupting the 224 values being processed to determine the correlation coefficients. The buffers 906, 908 may be simultaneously written and read which eases the computational burden on the microprocessor in the display device 600. The computation need not be completed in a single data sample time. Real word correlation is generally a serial process of mathematical operations. Each new correlation check is begun at the position of the last data written to the circular buffers 906, 908 and works backwards.

The correlation algorithm 902 may begin at the last data position written and work backwards through the data from this point. Based on the values of buffer size and assumed pulse rates, the complete computation must finish before 32 additional data samples are taken, that is: 32 samples/75 samples/second, or 0.43 seconds. In this time 112 sum-of-products are calculated. The sum-of-product, step 914, is the accumulation of 112 multiplications 910*a*-910*d* of data in each buffer 906, 908. Each correlation coefficient calculated at summation point 914 may be temporarily stored in an array buffer 918. Each value saved is the sum-of-product for 112 offsets of the $\tau$ parameter. The $\tau$ offset is the starting from which data is read from the buffers 906, 908 for each sum-of-product calculation. The array buffer 918 results may be analyzed to determine the degree of correlation between the pulsewaves. To normalize the cross-correlation results, auto-correlation may also be performed. Numerically, the cross-correlation results in buffer 918 should be values between +1.0 and −1.0. Values near 0.0 are considered to be non-correlated and indicated as not "In-Sync" on the display device 600. Values greater than a determined threshold are considered significantly correlated and provide an indication to the clinician of correct placement of the needle 302 and/or catheter 310. Should the pulse rate be greater than the minimum design value, multiple correlation coefficients will be produced. For example, at 80 BPM pulse rate, there will be 2 correlation maximums. The correlation algorithm 920 may analyze the data for maximum peak and generally select the τ offset value closer to zero. All of the selected correlation coefficients may be output to the display device 600. The analysis may include consideration of the measured BPM from each sensor 300, 400. BPM may also be obtained by analysis of the auto-correlation measurements made on each waveform 452, 453. Though possibly lacking in resolution detail, the separation measurement of multiple peaks in auto-correlation may be another measurement of pulse rates from each sensor 300, 400 and maybe useful information for making the correlation detection indication.

Controller Device Algorithm

Figure 8:
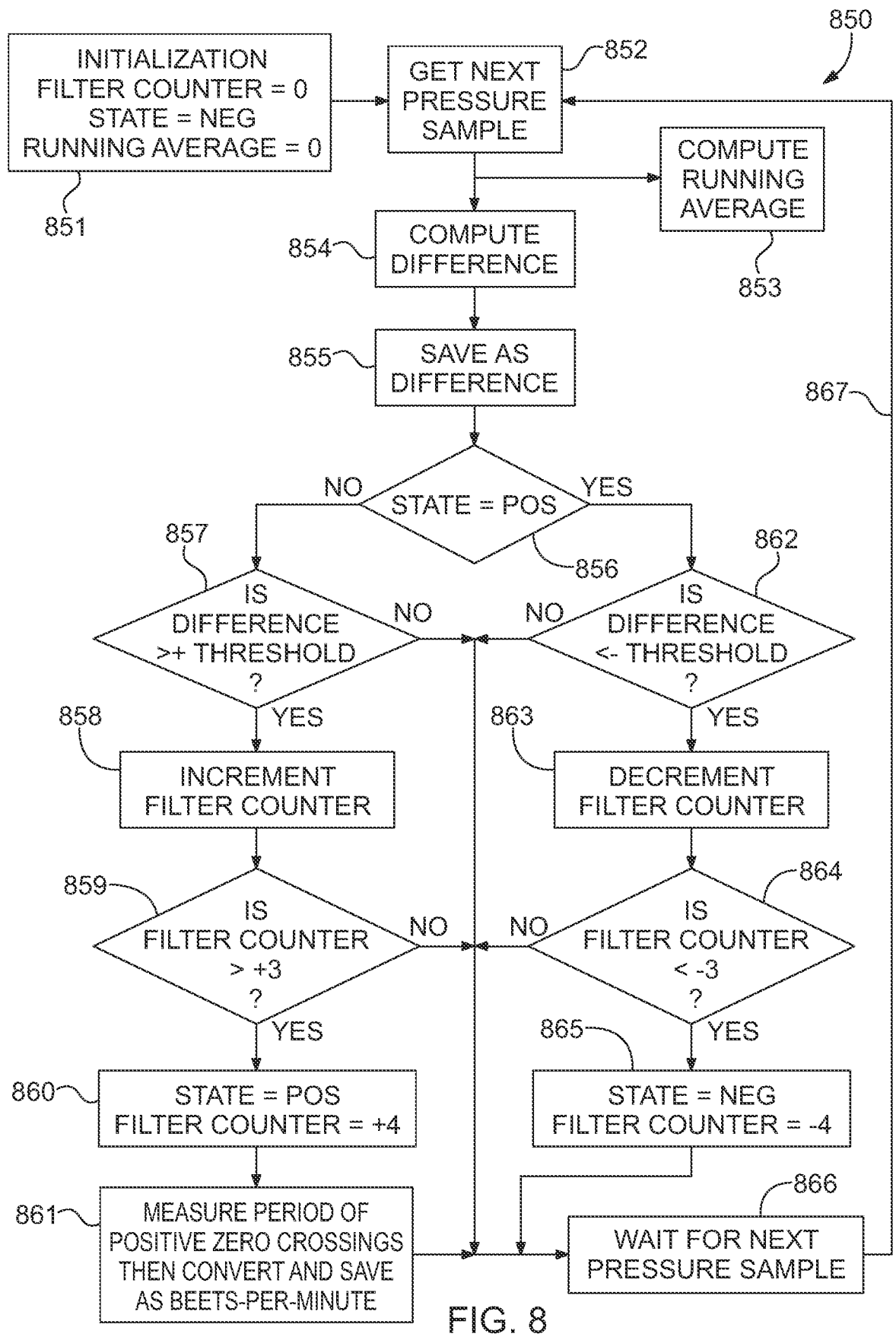
FIG. 8 illustrates a method for performing signal correlation in accordance with the present invention.

In another of its aspects, devices of the present invention may use the method 850 in confirming catheter or needle placement and patency, FIG. 8. The flowchart of FIG. 8 represents the software logic that was used in the prototype to calculate the beats-per-minute pulse rate as measured by the in-line pressure sensor 300. The software executed in the microprocessor U3, FIG. 6, of circuit 550 of the controller device 500. The software identified the zero-crossings of the cardiac pulsewave signal 452 in the needle 302 and/or catheter 310, FIG. 4. The beats-per-minute rate was determined by measuring the period of time between successive positive zero-crossings of the pulsewave signal 452. The positive zero-crossings were selected, because the ascending aortic systolic pressure wave has a faster rate of change and hence provides a more accurate point of measurement than the descending slope of the negative zero-crossings. The software operated in a loop 867 using a state machine to analyze the pulsewave 452.

The state machine was initialized at step 851 when software began executing, FIG. 8. The STATE variable determined which side of the mean average the loop 867 was last processing. A Filter Counter variable was provided which was incremented and decremented based on whether the difference between measured value and the mean average was above or below zero. The Running Average Filter was also initialized at step 851. At step 852, the pressure reading was obtained from the analog-to-digital converter U4 of FIG. 6. Analog-to-digital conversions were produced by hardware events and occurred at approximately 80 samples per second. A new value of the pressure sample was obtained at step 852 and was sent to the display device 600. The new pressure sample was also used in method 850. Specifically, the new pressure sample was added into the Running Average Filter by computing the running average at step 853. The Running Average Filter output a value which was the average of the last 128 pressure samples. At step 854 the pressure sample had the average value subtracted to generate the Difference value which was stored at step 855. Next, a decision was made at step 856 to determine if last previous operation was looking for a positive (POS) or negative (NEG) zero-crossing. If the STATE at step 856 was POS, then the software branched to step 862 looking for a negative crossing. The criterion for a negative crossing was that the Difference was less (more negative) than a negative threshold of −0.1 mmHg. If the Difference did not meet this criterion, then the loop passed to step 866 where it waited for the next pressure sample to repeat, via step 860, the processing of method 850. Returning to step 862, should the Difference meet the criterion, then the Filter Counter was decremented, step 863. At step 864 the count value was tested to determine if the count was less than −3. If not, control passed to step 866 and method 850 repeated by passing to step 866 and waiting for the next sample. Normally the last value of the Filter Counter would be +4 following the last positive zero-crossing. Hence the Filter Counter must be decremented 8 times to reach the value −4 tested, and the STATE variable was then set to NEG indicating that a descending zero-crossing was found, step 865. The Filter Counter value was forced such that it does not exceed −4. The loop 867 then returned to wait for the next pressure sample at step 866.

Returning to step 856, if the STATE at step 856 was NEG (i.e., not POS), that is looking for an ascending zero-crossing, the branch would continue to step 857. At step 857 a test was made to determine if the criterion for a positive zero-crossing was met. The Difference pressure must exceed +0.1 mmHg. If not, the method 850 repeated jumping to step 866 and waited for another pressure sample. Should the criterion be met, control passed to step 857. The Filter Counter value was incremented at step 858. Typically the counter would begin incrementing from −4 after the last descending zero-crossing. At step 859 the count value was tested to determine if sufficient positive differences had been found to justify indication of an ascending zero-crossing of pressure, that is that the count exceeded +3. If not, control passed to step 866 and method 850 repeated by passing to step 866 and waiting for the next sample. Should the Filter Counter exceed +3 at step 859, then control passed to step 860. At step 860 the STATE variable was set to POS and the Filter counter was limited to +4. At this point a valid positive zero-crossing had been determined. An algorithm measured the period of time since the last positive zero-crossing occurred. The period was measured in milliseconds by a time base maintained in microprocessor U3 using interrupts. The period measurement was dynamically adjusted to provide good BPM measurements. At fast heart rates greater than 200 BPM, up to 4 zero-crossings are counted to give a resolution better than 1.0 BPM. At low pulse rates, below 60 BPM, a single zero-crossing period measurement was performed to allow quicker updates of the measured heart rhythm. The final calculation of period was performed at step 861 and the calculated BPM value, 402 in FIG. 4, was sent to the process controller 600 for display to the user and for pulse correlation matching with the heart rate 404.

Figure 5:
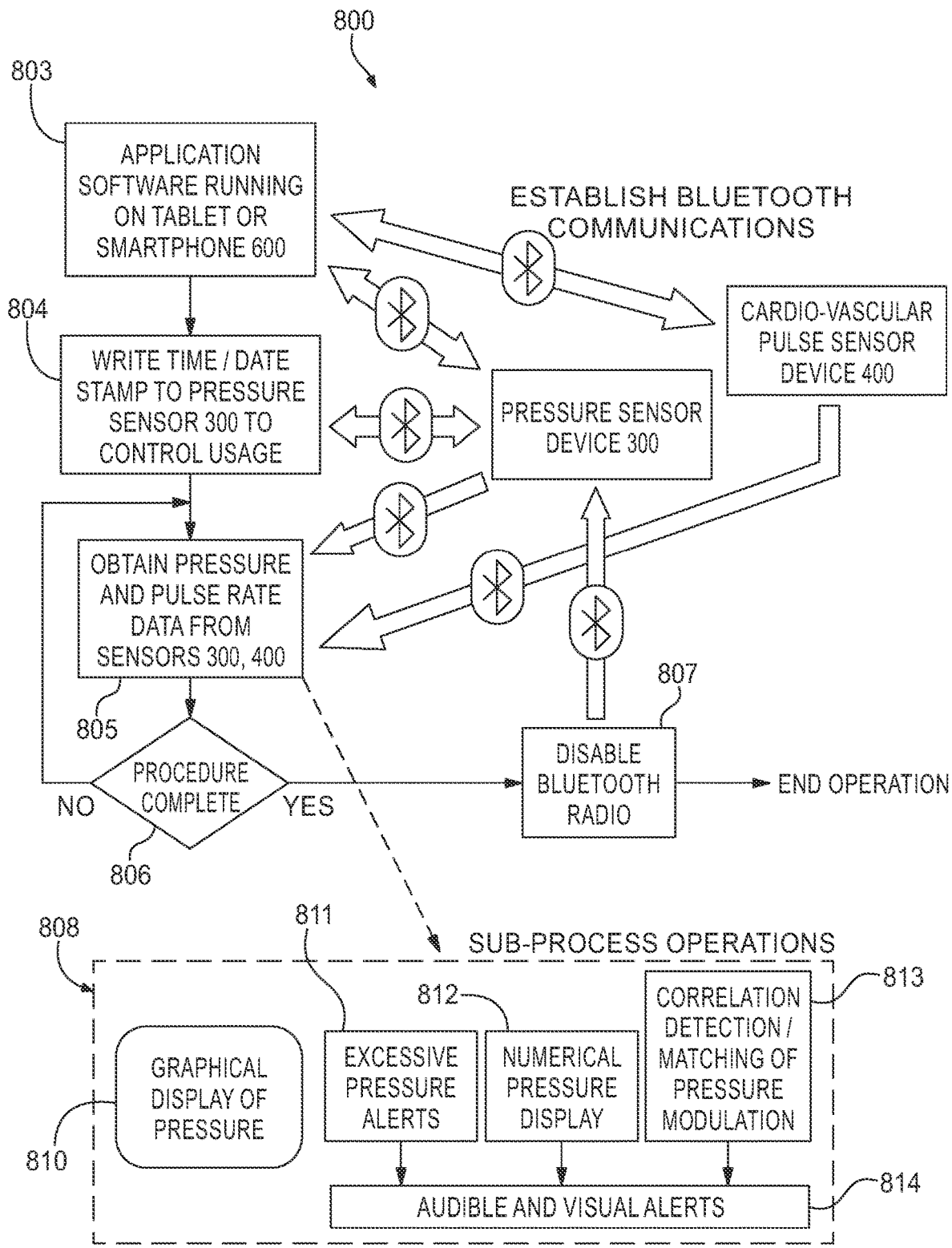
FIG. 5 schematically illustrates details of an exemplary operation of the devices of FIGS. 1-3.

A further understanding of how the devices 100, 150 of the present invention may operate with regard to generating the data for display on the display device 600 is seen in the block diagram 800 of FIG. 5. In this diagram, the "cardiovascular pulse sensor device" block corresponds to the sensor 400 and the "pressure sensor device" block corresponds to the sensor 300. Communication among the components and processes is illustrated as wireless using the conventional symbol for Bluetooth® communication, though the components and processes could communicate via other methods such as Wi-Fi or hard wired.

The application software 803, which can run on the display device 600, can include the step 804 for writing a time/date stamp to the sensor 300 to assist in ensuring that the sensor 300 is used for only a single use. As part of the operation, the software also obtains the data from the sensors 300, 400 at step 805. Collection of data continues until complete, step 806, and the Bluetooth® radio is disabled, step 807. During the data collection step 805 a sub process 808 can run which includes functions such as creating the graphical display of the pressure 810; calculating the excessive pressure alert 811; displaying the numerical pressure 812; performing the correlation detection of the data received from the sensors 300, 400, step 813; and, issuing the various alerts 814.

In addition, an authorization scheme of the present invention may include a computer chip, SIM, or other uniquely coded circuit in the adapter 212 or sensor 300, for example chip 320. The chip, SIM, or other uniquely coded circuit may be disposed in communication with the controller device 500 and/or display device 600, and may be read by an authorization program or circuit in the controller and/or display device 500, 600. If the chip, SIM, or other uniquely coded circuit is genuine, the controller and/or display device 500, 600 will operate properly, if not, the sensor 300 may be disabled and a warning such as "unauthorized adaptor detected" can be posted on the display device 600 and optionally a warning sound may be made, including but not limited to a vocalization of words, an alarm, or other warning signal or any combination thereof. The coded circuit may also be coded for a one-use function whereby the authorization program or circuit in controller and/or display device 500, 600 will detect if a specific sensor 300 was previously used and, if so, again disable the controller and/or display device 500, 600 and post a warning.

Description of an Exemplary Method

Figure 7:
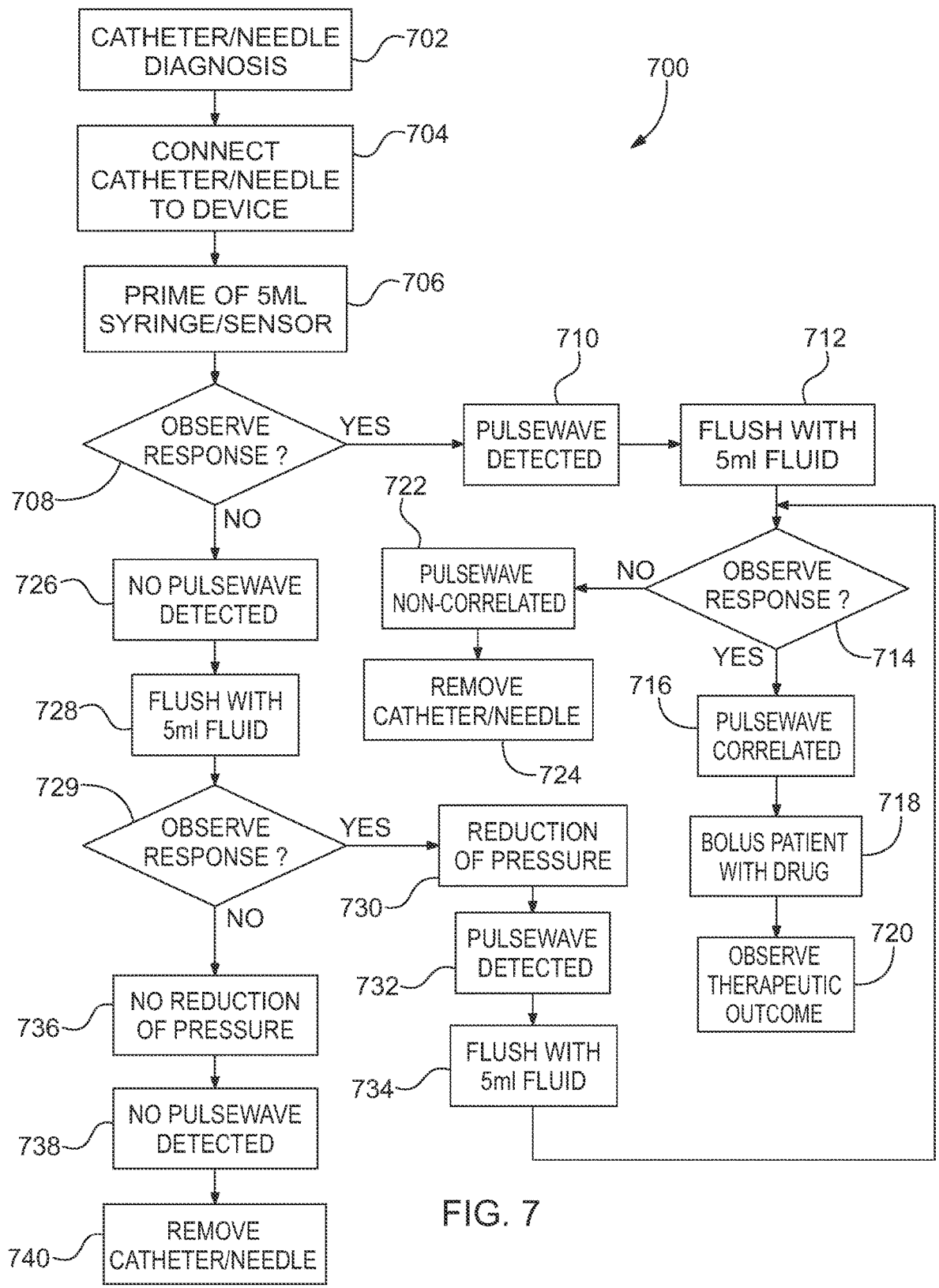
FIG. 7 illustrates a flow chart of an exemplary method of operating the device of the present invention.

In another of its aspects, devices of the present invention may provide the clinician with a particularly useful method of confirming catheter or needle placement and patency, such as the method 700 illustrated in FIG. 7. For example, the clinician often needs to determine if a catheter is: i) clogged or functioning and/or ii) if the catheter has moved from the target position, collectively beginning at step 702. Making such a determination may necessitate the following actions: 1) flush the catheter to determine if it is clogged or clear and then 2) infuse a bolus of drug. In making such a determination, the clinician may connect an in-line pressure sensor between the catheter and a syringe used to flush the catheter, step 704, and may attach a secondary input source to detect a heartbeat, such as a photophelthysmography fingertip clamshell to detect the heartbeat. The syringe and in-line pressure sensor, and any other disposables such as a catheter, may be primed with fluid, step 706. The in-line pressure sensor and secondary source may be operably connected, wired or wirelessly, to a display device for viewing by the clinician, step 708. A maximum objective pressure value may also be set on the handheld device and remain stored in the handheld device for future use. The maximum pressure value may be set anywhere between 75 mm/Hg to 500 mm/Hg, for example. When the maximum pressure value is reached an alert may be sounded as an audible sound or tone. A spoken word may also be used to alert the clinician that the maximum pressure has been exceeded.

Signals from the in-line pressure sensor and secondary source (e.g., a finger pulse sensor) may be compared and analyzed by a controller and/or display device, such as one or more of the controller 500 and display device 600. If the two signals are found to be correlated in frequency (that is beats-per-minute of a heartbeat), an alert may be displayed on the display device as a flashing box and/or an audible alert sounded, indicating that the catheter is properly positioned.

If a pulsewave is detected, step 710, the clinician may proceed with flushing the catheter, step 712. The clinician may again observe the response on the display device, step 714. If no response is observed and no pulsewave correlation is found between the signal from the in-line pressure sensor and the secondary input source, step 722, the pulsewave detected at step 710 (or step 732 as described below) is a false-positive finding. The clinician then concludes that the catheter is not properly positioned, and the catheter is removed, step 724. Alternatively, if a response is observed at step 714, and the clinician observes that pulsewave correlation is found between the signal from the in-line pressure sensor and the secondary input source, step 716, the clinician can bolus the patient with the drug, step 718, and observe the therapeutic output, step 720.

Returning to the situation where no initial response is observed at step 708, the clinician may observe the objective pressure graph to determine patency of the catheter. In such a case the clinician will likely see that no pulsewave is detected at all, step 726, but will still proceed with flushing the catheter, step 728. Again, the clinician may observe the response on the display device, step 729. The clinician may then determine if the catheter is clogged by observing an absence of a gradual reduction in the pressure; this may be observed by viewing an objective pressure vs. time graph in which the slope of the curve demonstrates whether fluid is flowing out of the catheter and into the tissues. If the pressure does not dissipate over time, step 736, and no pulsewave correlation is found between the signal from the in-line pressure sensor and the secondary input source, step 738, the clinician can conclude that the catheter is clogged and the catheter may be removed, step 740. Alternatively, if a response is observed at step 729 and the response is a reduction of pressure, step 730, the clinician may observe that pulsewave correlation is found between the signal from the in-line pressure sensor and the secondary input source, step 732. In such a case, the clinician may proceed with flushing the catheter, step 734, and may proceed with steps 714 through 724 as described above. The example in the proceeding sections describe the method for use with a catheter, it is understood that a similar method could be used for placement of a needle within a patient performed with the same steps described.

It is anticipated that the method 700 could be used for confirmation of the position of a catheter in the epidural space or the intrathecal space, for example. In addition, the method 700 could be used to determine when a needle or catheter is positioned properly in a vessel such as a vein or artery for an infusion. It is also conceivable that such a system could be used for aspiration of bodily fluids in which the needle position within a target confirmed by a pulsatile waveform is necessary prior to the removal of said fluid such as cerebral spinal fluid from the central nervous system. The method 700 may also be used in situations where assessing the pulsatile nature of a tissue is vital. Devices and methods of the present invention may also be used to assess the perfusion status of vessels to a tissue or organ based on the quality (amplitude and cadence) of the pulsatile pressure waveform as seen in the pulse interval and amplitude of the waveform curve; for example, the perfusion status may be assessed in the extremities as it relates to diabetes, frost-bite, trauma, tissue grafting, etc.

Thus, the above disclosure describes devices and methods that can confirm the location of a needle and/or catheter as well as the patency of properly located indwelling catheter. The devices and methods may provide essential confirmation through physiologic feedback that a needle or catheter has been positioned within an anatomic site. Devices in accordance with the present invention may detect the presence of cardiovascular signals from two separate input sources and determine if the signals are coordinated or not by analysis of the signals. A positive-correlation may be confirmed, verifying the position of a needle or catheter within the body and an alert may be provided in response. If a correlation cannot be established between the two cardiovascular signals, no alert is provided, which indicates that a needle and/or catheter is improperly positioned.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. For example, the apparatuses disclosed herein could incorporate a device to remotely monitor a patient, such as by Bluetooth, Wi-Fi or other device of transmitting the collected pressure data to the software loaded on a smartphone or computer workstation. The clinician would be able to assess the patient's condition related to the presence or absence of a pulsatile waveform. A communication module, optionally present in the controller device 500 and/or display device 600, may relay data collected to either an on-line external communication system or directly to a specific communication target to relay this information for either real-time or retrospective review. It should therefore be understood that this invention is not limited to the particular embodiments described herein, but is intended to include all changes and modifications that are within the scope and spirit of the invention as set forth in the claims.

What is claimed is:

1. An apparatus for confirming placement of a hollow-bore structure at a desired treatment location in a mammalian subject, comprising:
   a needle, a catheter or combination thereof to provide the hollow-bore structure, the hollow-bore structure having distal and proximal ends with respective openings thereat;
   a first sensor disposed in fluid communication with the hollow-bore structure;
   a syringe disposed in fluid communication with the first sensor, where each of the hollow-bore structure, first sensor, and syringe have a respective fluid passageway extending therethrough with all of the fluid passageways disposed in fluid communication to provide a continuous closed fluid pathway extending from the syringe through the first sensor to the opening at the distal end of the hollow-bore structure; and
   a controller configured to receive a first signal in response to detection of a first property from the first sensor, the first signal indicative of a cardiac pulse in the fluid passageway of the hollow-bore structure, the first signal also indicative of an objective pressure in the fluid passageway of the hollow-bore structure, and the controller configured to receive a second signal in response to detection of a second property indicative of the cardiac pulse from a second sensor placed at a second location, the controller programmed to compare the first and second signals to one another to determine if the first and second signals are correlated to provide a comparison result, whereby the comparison result provides an indication of placement of the hollow-bore structure relative to the desired treatment location.

2. The apparatus of claim 1, wherein the controller is programmed to provide an alert when the objective pressure exceeds a selected value indicative of an excess pressure in the fluid passageway of the hollow-bore structure.

3. The apparatus of claim 1, wherein the first sensor comprises an in-line pressure sensor disposed in fluid communication with the fluid passageway of the hollow-bore structure.

4. The apparatus of claim 1, wherein the second sensor comprises a finger pulse sensor.

5. The apparatus of claim 1, wherein the first property is one or more of a pressure, change in fluid volume, an electrical signal, and an optical signal.

6. The apparatus of claim 1, wherein the second property is one or more of a pressure, change in fluid volume, an electrical signal, and an optical signal.

7. The apparatus of claim 1, wherein the first and second properties relate to the same property.

8. The apparatus of claim 1, wherein the first and second properties relate to different physical properties.

9. The apparatus of claim 1, wherein the controller is disposed in wireless communication with one or more of the first and second sensors.

10. The apparatus of claim 1, wherein one or more of the first and second sensors includes a memory configured to store an indication that the first or second sensor, respectively, has been used.

11. The apparatus of claim 1, comprising an identification circuit embedded within or connected to one or more of the first and second sensors, wherein the identification circuit is configured to provide a signal to the controller, the signal including one or more of: a configuration signal indicative of physical characteristics of the first or second sensor; a verification signal indicative of the first or second sensor; and a use signal so that the controller can detect the number of times or length of time the first or second sensor was previously used.

12. The apparatus of claim 1, wherein the first signal represents one or more of a pressure, change in fluid volume, an electrical signal, and an optical signal.

13. The apparatus of claim 1, wherein the second signal represents one or more of a pressure, change in fluid volume, an electrical signal, and an optical signal.

14. The apparatus of claim 1, wherein the first signal has a first period and the second signal has a second period, and wherein the controller is configured to compare the first and second periods to provide the comparison result.

15. The apparatus of claim 1, wherein the first signal comprises a waveform having a first period and the second signal comprises a waveform having a second period, and wherein the controller is configured to compare the first and second periods to provide the comparison result.

16. The apparatus of claim 1, wherein the first signal comprises a first numeric value indicative of a frequency of the first signal, and the second signal comprises a second numeric value indicative of a frequency of the second signal, and wherein the controller is configured to compare the first and second numeric values.

17. The apparatus according to claim 16, wherein one or more of the first and second numeric values is a cardiac pulse in beats per minute.

18. The apparatus of claim 1, wherein one or more of the first and second signals each comprise a respective waveform having a respective period and having a respective mean value, and wherein the controller is configured to detect zero-crossings of each of the respective waveforms through the respective mean value.

19. The apparatus of claim 1, wherein the controller is configured to create an alert signal when the comparison result is within a selected range.

20. The apparatus of claim 1, comprising a display operably connected to the controller for receiving one or more of the first and second signals and the comparison result from the controller.

21. The apparatus of claim 20, wherein the controller includes the display.

22. The apparatus of claim 20, wherein the display includes a first data section for displaying a pressure versus time in the lumen of the hollow-bore structure.

23. The apparatus of claim 20, wherein the display includes a second data section for displaying the first and second signals.

24. The apparatus of claim 23, wherein the first and second signals each include a respective waveform, and wherein the second data section includes a graph displaying as a function of time the respective waveforms of the first and second signals.

25. The apparatus of claim 20, wherein the display includes a section for displaying an alert indication when the comparison result is within a selected range.

26. The apparatus of claim 25, wherein the alert is one or more of an auditory, visual, and haptic signal.

27. The apparatus of claim 1, wherein the controller is programmed to perform a cross-correlation analysis of the first and second signals.

28. The apparatus of claim 1, wherein the comparison result does not include comparing different respective portions of the first signal.

29. The apparatus of claim 28, wherein controller is programmed to determine that the first and second signals are correlated by using a cross-correlation of the sum of the product of the first and second signals.

30. The apparatus of claim 1, wherein controller is programmed to determine that the first and second signals are correlated at a fundamental frequency in the presence of a phase offset between the first and second signals.

31. The apparatus of claim 27, wherein the cross-correlation function is $$(f*g)(\tau) \triangleq \sum_{t0}^{t0+T} \overline{f(t-\tau)} g(t) dt,$$

where T is the period (number of samples) of the waveform being analyzed, t is the sliding offset between the two waveforms, f is the first signal, and g is the second signal.

32. A method for a clinician to confirm catheter or needle placement and patency in a patient, comprising:
providing the apparatus of claim 1;
connecting the first sensor between the hollow-bore structure and the syringe, and using the syringe to flush the hollow-bore structure;
receiving the first signal from the first sensor to detect a first property indicative of a cardiac pulse in the lumen of the hollow-bore structure;
attaching the second sensor to the patient;
receiving the second signal from the second sensor to detect a second property indicative of the cardiac pulse;
operably connecting the first and second sensors to the controller;
comparing first and second signals using the controller to determine if the signals are correlated with a frequency of the heartbeat of the patient; and
sending an alert to the controller in response to a determination that the compared signals are correlated with a frequency of the heartbeat of the patient.

33. A method for a clinician to confirm catheter or needle placement and patency in a patient, comprising:
connecting an in-line pressure sensor between a catheter and a syringe that is used to flush the catheter;
attaching a secondary input source to the patient to detect a heartbeat;
priming the syringe and catheter with a fluid;
operably connecting the in-line pressure sensor and secondary input source to a controller;
comparing signals from the in-line pressure sensor and secondary input source using the controller to determine if the signals are correlated with a frequency of the heartbeat of the patient; and
sending an alert to the controller in response to a determination that the compared signals are correlated with a frequency of the heartbeat of the patient.

* * * * *